United States Patent
Afonina et al.

(10) Patent No.: US 11,590,080 B2
(45) Date of Patent: *Feb. 28, 2023

(54) DRUG-LOADED BIODEGRADABLE MICROBEAD COMPOSITIONS INCLUDING DRUG-CONTAINING VESICULAR AGENTS

(71) Applicant: C.R. Bard, Inc., Tempe, AZ (US)

(72) Inventors: Elena Afonina, Franklin Lakes, NJ (US); Hiep Do, Franklin Lakes, NJ (US); Emily Goel, Franklin Lakes, NJ (US); Oleg Guryev, Franklin Lakes, NJ (US); Cyal Lecy, Franklin Lakes, NJ (US); Majid Mehrpouyan, Franklin Lakes, NJ (US); Michael Randall, Franklin Lakes, NJ (US); Marybeth Sharkey, Franklin Lakes, NJ (US); Jeffrey Wang, Franklin Lakes, NJ (US)

(73) Assignee: C.R. Bard, Inc., Franklin Lakes, NJ (US)

( * ) Notice: Subject to any disclaimer, the term of this patent is extended or adjusted under 35 U.S.C. 154(b) by 100 days.

This patent is subject to a terminal disclaimer.

(21) Appl. No.: 16/913,314

(22) Filed: Jun. 26, 2020

(65) Prior Publication Data

US 2021/0052499 A1  Feb. 25, 2021

Related U.S. Application Data

(63) Continuation-in-part of application No. 16/955,275, filed as application No. PCT/US2018/066232 on Dec.
(Continued)

(51) Int. Cl.
*A61K 9/16* (2006.01)
*A61K 31/4412* (2006.01)
(Continued)

(52) U.S. Cl.
CPC ............ *A61K 9/1652* (2013.01); *A61K 9/127* (2013.01); *A61K 9/146* (2013.01); *A61K 9/19* (2013.01);
(Continued)

(58) Field of Classification Search
CPC .............................. A61K 9/1652; A61K 9/127
See application file for complete search history.

(56) References Cited

U.S. PATENT DOCUMENTS 6,676,971 B2  1/2004  Goupil et al.
7,507,772 B2  3/2009  Baldwin et al.
(Continued)

FOREIGN PATENT DOCUMENTS

CN    101889985 A    11/2010
CN    102159247 A    8/2011
(Continued)

OTHER PUBLICATIONS

International Search Report and Written Opinion dated May 14, 2019 in related International Application No. PCT/US2018/066232.
(Continued)

*Primary Examiner* — Carlos A Azpuru
(74) *Attorney, Agent, or Firm* — Dinsmore & Shohl LLP

(57) ABSTRACT

Drug-loaded microbead compositions include microbeads of a biodegradable material and vesicular agents located within or associated with the biodegradable material of the microbeads. The vesicular agents include a lipid bilayer and comprise liposomes or ethosomes. The drug-loaded microbeads include a first therapeutic agent associated with the vesicular agents, and a second therapeutic agent different from the first therapeutic agent. The vesicular agents include a lipid bilayer surrounding a vesicular core. The second therapeutic agent is contained within the microbeads or associated with the microbeads through ionic or non-cova-
(Continued)

lent interaction and may or may not be associated with the vesicular agents. Drug-loaded biodegradable microbead compositions include microbeads of biodegradable material and a therapeutic agent.

11 Claims, 1 Drawing Sheet

Related U.S. Application Data 18, 2018, application No. 16/913,314, which is a continuation-in-part of application No. PCT/US2019/037984, filed on Jun. 19, 2019.

(60) Provisional application No. 62/607,080, filed on Dec. 18, 2017.

(51) Int. Cl.
*A61K 9/19* (2006.01)
*A61K 9/14* (2006.01)
*A61K 9/127* (2006.01)
*A61K 31/704* (2006.01)

(52) U.S. Cl.
CPC ........ *A61K 31/4412* (2013.01); *A61K 31/704* (2013.01)

(56) References Cited

U.S. PATENT DOCUMENTS

| | | |
|---|---|---|
| 8,012,454 B2 | 9/2011 | Rioux et al. |
| 8,216,612 B2 | 7/2012 | DiCarlo et al. |
| 8,221,793 B2 | 7/2012 | Lewis et al. |
| 8,287,840 B2 | 10/2012 | Zhang et al. |
| 8,414,927 B2 | 4/2013 | Richard |
| 8,445,022 B2 | 5/2013 | DiCarlo et al. |
| 8,455,003 B2 | 6/2013 | Lewis et al. |
| 8,586,098 B2 | 11/2013 | Lewis et al. |
| 8,617,132 B2 | 12/2013 | Golzarian et al. |
| 8,685,367 B2 | 4/2014 | Brandom et al. |
| 8,697,137 B2 | 4/2014 | Vogel et al. |
| 8,992,993 B2 | 3/2015 | Richard |
| 9,339,591 B2 | 5/2016 | DiCarlo et al. |
| 9,526,804 B2 | 12/2016 | O'Gara |
| 2001/0014354 A1 | 8/2001 | Yokoyama et al. |
| 2004/0241094 A1 | 12/2004 | Chung et al. |
| 2006/0177513 A1 | 8/2006 | Martin et al. |
| 2009/0053318 A1 | 2/2009 | Tan et al. |
| 2011/0104052 A1 | 5/2011 | Barnett et al. |
| 2011/0212179 A1 | 9/2011 | Liu |
| 2015/0150801 A1 | 6/2015 | Park et al. |
| 2015/0224221 A1 | 8/2015 | Lee et al. |
| 2015/0231069 A1 | 8/2015 | Modi |
| 2015/0314020 A1 | 11/2015 | Reb |
| 2016/0220490 A1 | 8/2016 | Zeng et al. |
| 2017/0189569 A1 | 7/2017 | Souresrafil et al. |

FOREIGN PATENT DOCUMENTS

| | | |
|---|---|---|
| EP | 2891485 A2 | 7/2015 |
| JP | 2000516246 A | 12/2000 |
| JP | 2001226294 A | 8/2001 |
| JP | 2004530768 A | 10/2004 |
| JP | 2015526510 A | 9/2015 |
| WO | 9807434 A1 | 2/1998 |
| WO | 03000778 A1 | 1/2003 |
| WO | 2009073193 A2 | 6/2009 |
| WO | 2009137689 A2 | 11/2009 |
| WO | 2009137689 | * 12/2009 |
| WO | 2010014117 A1 | 2/2010 |
| WO | 2012101455 A1 | 8/2012 |
| WO | 2017031060 A1 | 2/2017 |
| WO | 2018064150 A1 | 4/2018 |
| WO | 2018218208 | * 11/2018 |
| WO | 2018218208 A1 | 11/2018 |

OTHER PUBLICATIONS

International Search report and Written Opinion dated Mar. 30, 2020 in related International Application No. PCT/US2019/037984.
International Preliminary Report on Patentability dated Jun. 23, 2020 in related International Application No. PCT/US2018/066232.
Babos, et al., "Dual Drug Delivery of Sorafenib and Doxorubicin from PLGA and PEG-PLGA Polymeric Nanoparticles", MDPI polymers, vol. 10, pp. 1-12, 2018.
Duan, et al., "Targeted and synergistic therapy for hepatocellular carcinoma: monosaccharide modified lipid nanoparticles for the co-delivery of doxorubicin and sorafenib", Drug Design, Development and Therapy, vol. 12, pp. 2149-2161, 2018.
Ye, et al., "Low-density lipoprotein decorated silica nanoparticles co-delivering sorafenib and doxorubicin for effective treatment of hepacellular carcinoma", Drug Delivery, vol. 25, No. 1, pp. 2007-2014, 2018.
Raval, et al., "Thermodynamic and Spectroscopic Studies on the Molecular Interaction of Doxorubicin (DOX) with negatively charged Polymeric Nanoparticles", Graduate department of Pharmaceutical Sciences, pp. 1-79, 2012.
Hecq, et al., "Doxorubicin-loaded drug-eluting beads (DC Bead) for use in transarterial chemoembolization: A stability assessment", Journal of Oncology Pharmacy Practice, vol. 19, pp. 65-74, 2012.
Baere, et al., "An In Vitro Evaluation of Four Types of Drug-Eluting Microspheres Loaded with Doxorubicin", Laboratory Investigation, pp. 1425-1431, 2016.
China National Intellectual Property Administration First Search Report dated Jan. 24, 2022 in related Chinese Application for Invention No. 201880088282.1.
Niu, et al., "Hydrogel loaded with self-assembled dextran sulfate-doxorubicin complexes as a delivery system for chemotherapy", Materials Science and Engineering C, Apr. 3, 2017, pp. 888 894, vol. 77, Elsevier.
Japanese Office Action dated Aug. 19, 2022 pertaining to JP Application No. 2020-533787 filed Jun. 18, 2020.

* cited by examiner

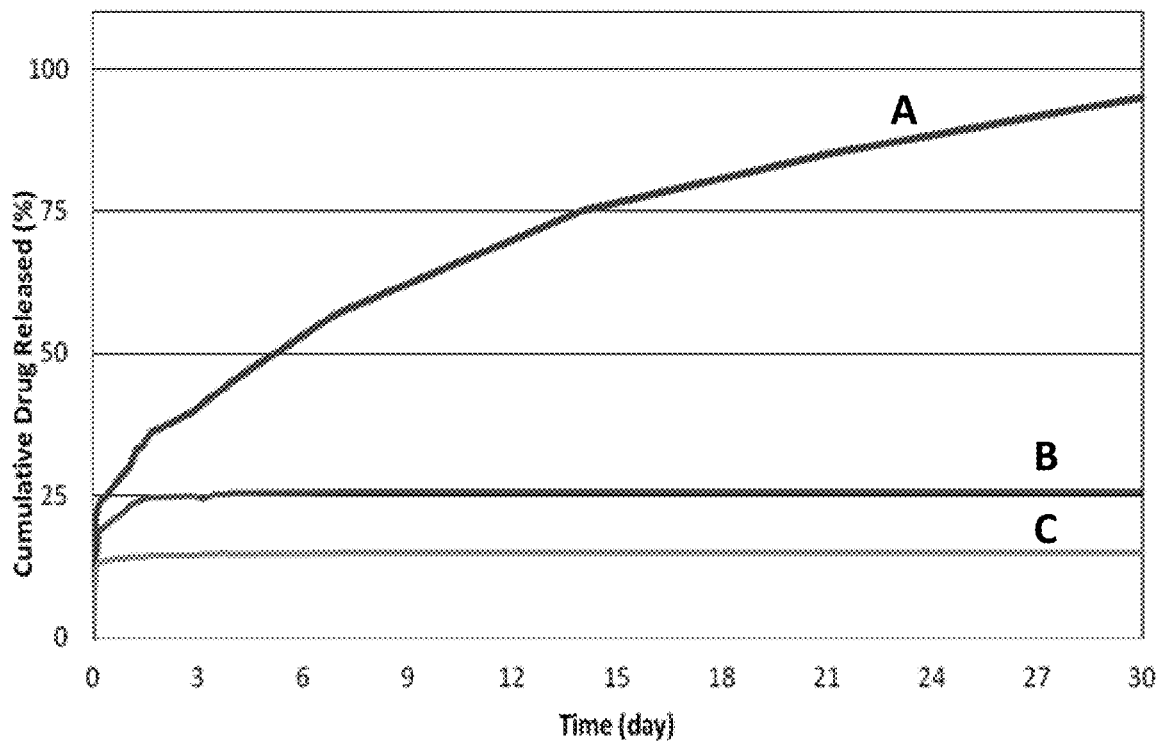

DRUG-LOADED BIODEGRADABLE MICROBEAD COMPOSITIONS INCLUDING DRUG-CONTAINING VESICULAR AGENTS

CROSS-REFERENCES TO RELATED APPLICATIONS

The present application is a continuation-in-part of U.S. application Ser. No. 16/955,275, filed Jun. 18, 2020, which is a national-phase application of International Application No. PCT/US2018/066232, filed Dec. 18, 2018, which claims the benefit of priority to U.S. Provisional Application Ser. No. 62/607,080, filed Dec. 18, 2017, the present application being also a continuation-in-part under 35 U.S.C. §§ 111(a) of International Application No. PCT/US2019/037984 designating the United States, filed Jun. 19, 2019. All of the foregoing priority documents are hereby incorporated by reference into this disclosure in their entireties.

TECHNICAL FIELD

This disclosure relates to microbeads for chemoembolization, to methods for preparing the microbeads, to methods for using the microbeads, and to biodegradable drug-eluting particles containing therapeutic agents for chemoembolization.

BACKGROUND

Embolization therapy is a minimally invasive surgery performed by interventional radiologists. Typical treatments may include entering the vasculature via a minor incision, such as in the arm or leg, and gaining access to the treatment site by use of guidewires and catheters, optionally aided by imaging techniques such as fluoroscopy. The embolic agent at the treatment site embolizes the vessel, blocking off the flow of blood to tumors downstream from the treatment site and resulting in necrosis and/or shrinkage of the tumors.

The embolic agent of choice for embolization therapy depends on the desired clinical outcome, as well as the inherent properties of the embolic agent. Embolic agents used clinically suffer common drawbacks. First, the embolic agents are provided without preloaded drug, meaning that the physician must order a pharmacy to load the drug into the embolic agent well in advance of surgery, typically at least 24 hours before the surgery. Second, the embolic agents have a suboptimal pharmacokinetic release profile that stops releasing drug into the target treatment site after only a few days after implantation, typically within about 3 days after implantation.

Among the diseases for which embolization therapy may be effective is hepatocellular carcinoma (HCC). Hepatocellular carcinoma accounts for 80% to 90% of all primary liver cancers. The mortality of hepatocellular carcinoma is high, and treatment options are limited. Patients with cirrhosis exhibit a high probability of developing hepatocellular carcinoma.

Sorafenib (co-developed and co-marketed by Bayer and Onyx Pharmaceuticals as Nexavar) is an orally administered kinase inhibitor drug approved for the treatment of primary kidney cancer (advanced renal cell carcinoma), radioactive iodine resistant advanced thyroid carcinoma, and advanced primary liver cancer such as hepatocellular carcinoma. With the exception of sorafenib tosylate (the toluene salt of sorafenib), no targeted agent is currently approved for the treatment of hepatocellular carcinoma.

Cytotoxic agent doxorubicin exhibits a broad spectrum of antitumor activity. When administered via the hepatic artery, doxorubicin exhibits antitumor effects and partial response in hepatocellular carcinoma patients. An exploratory analysis of a randomized phase II study in hepatocellular carcinoma comparing doxorubicin alone to doxorubicin plus sorafenib showed a significant improvement in overall survival favoring the combination.

Ongoing needs exist for embolic agents and embolization therapy methods that enable greater efficiency in preparation of the embolic agents and that also provide sustained, longer-term delivery of therapeutic agent to the embolization site.

Ongoing needs exist for embolic agents and embolization therapy methods that enable greater efficiency in preparation of the embolic agents and that also provide sustained, longer-term delivery of therapeutic agent to the embolization site. Furthermore, ongoing needs exist for embolic agents that are capable of delivering multiple therapeutic agents, including but not limited to the combination of sorafenib and doxorubicin, in a controlled manner as an alternative to oral administration.

SUMMARY

Accordingly, embodiments of this disclosure include drug-loaded microbead compositions, methods for preparing the drug-loaded microbead compositions, embolization compositions prepared from the drug-loaded microbead compositions, methods for preparing the embolization compositions, and methods for treating diseases with the embolization compositions.

According to embodiments, a drug-loaded microbead composition may include microbeads comprising a water-swellable polymer material; and a complex comprising a carrier and a therapeutic agent chemically bonded to the carrier. In the drug-loaded microbead compositions, the complex is embedded within the polymer material. The drug-loaded microbead composition have a water content of less than 1% by weight, based on the total weight of the drug-loaded microbead composition.

According to embodiments, methods for preparing a drug-loaded microbead composition may include dissolving a carrier and a therapeutic agent in an aqueous solvent to form an initial mixture, the initial mixture comprising a complex of the carrier and the therapeutic agent. The methods may further include combining the initial mixture with a first solvent composition in which the therapeutic agent is less soluble than in the aqueous solvent to form a second mixture, and stirring the second mixture rapidly to form particles of the complex in the second mixture. The methods may further include combining the particles of the complex with a hydrogel of a water-swellable polymer material to form a hydrogel mixture; combining the hydrogel mixture with a second solvent composition to form a synthesis mixture; stirring the synthesis mixture rapidly to form drug-loaded microbeads in the synthesis mixture; and recovering the drug-loaded microbeads from the synthesis mixture. The methods may further include removing water from the drug-loaded microbeads to form a drug-loaded microbead composition having a water content of less than 1% by weight, based on the total weight of the drug-loaded microbeads in the drug-loaded microbead composition.

According to embodiments, methods for preparing a drug-loaded microbead composition may include dissolving a carrier and a therapeutic agent in an aqueous solvent to form an initial mixture, the initial mixture comprising a complex of the carrier and the therapeutic agent; combining the initial mixture with a hydrogel solution of a water-swellable polymer material to form a hydrogel mixture; combining the hydrogel mixture with a solvent composition to form a synthesis mixture; stirring the synthesis mixture rapidly to form drug-loaded microbeads in the synthesis mixture; and recovering the drug-loaded microbeads from the synthesis mixture. The methods may further include drying the drug-loaded microbeads to form a drug-loaded microbead composition having a water content of less than 1% by weight, based on the total weight of the drug-loaded microbeads in the drug-loaded microbead composition.

According to embodiments, an embolization composition may include a drug-loaded microbead composition according to any embodiment of this disclosure, in combination with an amount of an aqueous solution sufficient to cause the drug-loaded microbeads of the drug-loaded microbead composition to swell. In the embolization compositions, the drug-loaded microbeads after swelling comprise a water content of from 50% by weight to 95% by weight, based on the total weight of the drug-loaded microbeads.

According to embodiments, methods for preparing an embolization composition may include adding a drug-loaded microbead composition according to any embodiment of this disclosure, or a drug-loaded microbead composition made according to the method of preparing the drug-loaded microbead composition according any embodiment of this disclosure, to an amount of an aqueous solution sufficient to cause the drug-loaded microbeads of the drug-loaded microbead composition to swell and form an injection-ready solution. In the embolization solution made according to such methods, the drug-loaded microbeads after swelling have a water content of from 50% by weight to 95% by weight, based on the total weight of the drug-loaded microbeads. The methods may further include loading the injection-ready solution into an injection device.

According to embodiments, methods for treating a disease may include providing intravenously, to a subject in need of embolization therapy, an embolization composition according to any embodiment of this disclosure.

Further embodiments are directed to drug-loaded microbead compositions including a plurality of individual microbeads of a biodegradable material, a plurality of individual vesicular agents, a first therapeutic agent, and a second therapeutic agent different from the first therapeutic agent. The vesicular agents include at least one lipid bilayer surrounding a vesicular core. The first therapeutic agent is associated with the individual vesicular agents. For example, the first therapeutic agent may be contained within the individual vesicular agents or may be associated with the individual vesicular agents by ionic or non-covalent interaction. The second therapeutic agent is different from the first therapeutic agent, is contained within the individual microbeads or associated with the individual microbeads through ionic or non-covalent interaction, and may or may not be associated with the individual vesicular agents within the individual microbeads.

Example embodiments disclosed herein are directed to methods for preparing the drug-loaded microbead compositions, to embolization compositions prepared from the drug-loaded microbead compositions, to methods for preparing the embolization compositions, and to methods for treating a disease using the embolization compositions.

Further embodiments of this disclosure are directed to drug-loaded biodegradable microbead compositions. The drug-loaded biodegradable microbead compositions may include microbeads of a biodegradable material and at least one therapeutic agent embedded in a matrix of the biodegradable material, encapsulated by a matrix of the biodegradable material, disposed within a porous structure formed by the matrix of the biodegradable material, or ionically or non-covalently associated with a matrix of the biodegradable material. In such embodiments of drug-loaded biodegradable microbead compositions, the microbeads of the biodegradable material may contain, but need not necessarily contain, vesicular agents such as liposomes or ethosomes.

BRIEF DESCRIPTION OF THE DRAWING

The FIGURE is a graph of in vivo drug release vs. time for (A) drug-loaded microbeads in an embolization composition according to one or more embodiments of this disclosure; (B) a comparative embolization composition containing microbeads of biocompatible sulfonate-modified poly(vinyl alcohol) (PVA) loaded with doxorubicin; and (C) a comparative embolization composition containing microbeads of a sodium acrylate alcohol copolymer formed by polymerization of vinyl acetate and methyl acrylate and loaded with doxorubicin.

Additional features and advantages of the embodiments described herein will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Some embodiments of this disclosure are directed to drug-loaded microbead compositions, to methods for preparing the drug-loaded microbead compositions, to embolization compositions prepared from the drug-loaded microbead compositions, to methods for preparing the embolization compositions, and to methods for treating a disease using the embolization compositions. The drug-loaded microbead compositions include microbeads into which a therapeutic agent has been pre-loaded. When included in an embolization composition and provided to a subject as part of an embolization therapy, the embolization compositions may provide a continuous release of the drug into the target treatment site for at least 7 days, at least 14 days, at least 21 days, or at least 30 days after implantation.

A drug-loaded microbead composition may include microbeads loaded with a therapeutic agent or with a complex of a therapeutic agent and a carrier. The microbeads may be beads or microparticles of a water-swellable polymer material, such as a polymer material capable of forming a hydrogel.

In the microbeads of the drug-loaded microbead composition, the therapeutic agent or complex of the therapeutic agent may be embedded within the water-swellable polymer materials. Except when described otherwise, the term "embedded" broadly includes embodiments for which the water-swellable polymer material or some portion thereof generally surrounds the therapeutic agent or the complex including the therapeutic agent or is embedded by the therapeutic agent or the complex including the therapeutic agent. For example, "embedded" may include in some embodiments a water-soluble polymer material shell that encapsulates a core that holds the therapeutic agent or complex. In other embodiments, "embedded" may include a structure in which the therapeutic agent or the complex is physically disposed within a matrix, network, or pore structure of a water-swellable polymer material that may or may not have a core within an outer shell. The therapeutic agent itself is not chemically bonded to the water-swellable polymer material at all or is not chemically bonded directly to the polymer backbone of the water-swellable polymer material. The drug-loaded microbead composition may have a water content of less than 1% by weight, based on the total weight of the drug-loaded microbead composition.

In various embodiments, the water-swellable polymer material of the drug-loaded microbead composition may include a natural hydrogel polymer such as a chitosan or a polysaccharide, or a synthetic hydrogel polymer such as a polyacrylate, a polyamide, a polyester, a polysaccharide, a poly(methylmethacrylate), or a poly(vinyl alcohol), for example. In some embodiments, the water-swellable polymer material may be biodegradable. Specific examples of water-swellable polymer materials include, without limitation, poly(-hydroxybutyrate), methacrylated hyaluronic acids (hyaluronic acids being polymers of disaccharides composed of D-glucuronic acid and N-acetyl-D-glucosamine), chitosan-alginates, poly(N-isopropylacrylamide) copolymers, poly(N-isopropylacrylamide)-alginates, poly(N-isopropylacrylamide)-peptides, poly(N-isopropylacrylamide)-α-acryloyloxy-β,β-dimethyl-γ-butyrolactone-hydrophilic Jeffamine, or poly(N-isopropyl-acrylamide)-poly(ethylene glycol) diacrylate-pentaerythritol tetrakis(3-mercapto-propionate). The water-swellable polymer materials of the drug-loaded microbead composition may include derivatives of any of the foregoing materials, or may include combinations of any of the foregoing materials or their derivatives. For example, the drug-loaded microbead compositions may include a combination of multiple water-swellable polymer materials, in which each individual microbead is made of a single type of polymer, and the drug-loaded microbead composition includes microbeads of multiple polymer types. Alternatively, the drug-loaded microbead compositions may include a combination of multiple water-swellable polymer materials, in which individual microbeads of the composition are composed of multiple types of polymer.

The drug-loaded microbead composition includes a therapeutic agent. In some embodiments, the therapeutic agent may be a hydrophilic therapeutic agent or a therapeutic agent that either is water soluble or has at least some solubility in an aqueous solution. In some embodiments, the therapeutic agent may be a chemotherapeutic agent having at least some efficacy for treating a disease such as cancer. In some embodiments, the therapeutic agent may be a chemotherapeutic agent having at least some efficacy for treating a cancer such as hepatocellular carcinoma, liver cancer, prostate cancer, or breast cancer. The therapeutic agent may have one or more chemical moieties or atomic centers having a positive or negative charge or affinity. Examples of specific therapeutic agents include, without limitation, doxorubicin, sorafenib, vandetanib, nivolumab, ipilimumab, regorafenib, irinotecan, epirubicin, pirarubicin, 5-fluorouracil, cisplatin, floxuridine, mitomycin C, derivatives of any of the foregoing, prodrugs of any of the foregoing, therapeutically acceptable salts or crystalline forms of any of the foregoing, or combinations of any of the foregoing. Further examples of suitable therapeutic agents include, without limitation, pirarubicin, mitoxantrone, tepotecan, paclitaxel, carboplatin, pemetrexed, penistatin, pertuzumab, trastuzumab, and docetaxel.

Individual microbeads of the drug-loaded microbead composition may include one therapeutic agent or a plurality of therapeutic agents. Collectively, the microbeads of the drug-loaded microbead composition may include some microbeads loaded with one specific therapeutic agent or combination of specific therapeutic agents and other microbeads loaded with a different specific therapeutic agent or combination of specific therapeutic agents.

In some embodiments, the therapeutic agent of the drug-loaded microbead composition may be embedded within the microbeads of the water-swellable polymer material but not chemically bonded to the water-swellable polymer material. In some embodiments, the therapeutic agent of the drug-loaded microbead composition may be embedded within the microbeads of the water-swellable polymer material and not chemically bonded directly to the polymer backbone water-swellable polymer material, yet may be chemically bonded to a functional group of the water-swellable polymer material. As used herein, "not chemically bonded" refers to a lack of covalent chemical bonds between the therapeutic agent and the water-swellable polymer but does not preclude the existence of noncovalent intermolecular interactions such as ionic interactions or a van der Waals interaction between the therapeutic agent and the water-swellable polymer material.

In some embodiments, the drug-loaded microbead composition includes a complex of a carrier and a therapeutic agent. In the complex, the therapeutic agent may be chemically bonded to the carrier or may be associated with the carrier by a non-covalent means such as encapsulation or a van der Waals interaction. The complex may be embedded within the water-swellable polymer material. When the complex is embedded within the microbeads, the carrier may be chemically bonded to the water-swellable polymer material while the therapeutic agent is not chemically bonded to the water-swellable polymer material. Without intent to be bound by theory, it is believed that when the therapeutic agent is bonded or associated with the carrier but is not chemically bonded to the water-swellable polymer material, the microbeads of the drug-loaded microbead composition are less susceptible to shrinking as a result of replacing water molecules with drug molecules during drug loading. Accordingly, the final size distribution of the drug-loaded microbeads can be controlled more readily by selecting appropriate microbead sizes before the therapeutic agent is loaded.

When the drug-loaded microbead composition includes a complex of the carrier and the therapeutic agent, the carrier may be any pharmaceutically acceptable compound that can complex with or encapsulate the therapeutic agent. In some embodiments, the carrier may have charged chemical groups or chemical groups with dipole moments that interact with corresponding chemical groups of the therapeutic agent having an opposite charge or opposite dipole moment. If the carrier is a polymeric material, the carrier is a different material from the water-swellable polymer material. Non-limiting examples of suitable carriers include polysaccharides, liposomes, polymeric micelles, Pluronics, polycaprolactone-b-methoxy-PEG, poly(aspartic acid)-b-PEG, poly (benzyl-L-glutamate)-b-PEG, poly(D,L-lactide)-b-methoxy-PEG, poly(β-benzyl-L-asparate)-b-PEG). Non-limiting examples of polysaccharides include dextrans and dextran sulfates such as dextran sodium sulfate. In one example embodiment, the carrier may include a dextran sodium sulfate having a weight-average molecular weight of from about 40 kDa (kilodalton) to about 500 kDa, or from about 50 kDa to about 300 kDa, or from about 100 kDa to about 300 kDa, or about 100 kDa to about 200 kDa.

The drug-loaded microbead compositions according to embodiments may have a very low water content such as less than 1%, or less than 0.1%, or less than 0.05% (500 ppm), or less than 0.02% (200 ppm), or less than 0.01% (100 ppm), or less than 0.005 (50 ppm), or less than 0.002% (20 ppm), or less than 0.001% (10 ppm) by weight water, based on the total weight of the microbeads in the drug-loaded microbead composition. Without intent to be bound by theory, it is believed that a very low water content of the drug-loaded microbead composition increases the shelf-life and long-term stability of the drug-loaded microbead composition. Further, it is believed that water contents significantly greater than 1% by weight (such as 2%, 3%, 5%, or 10%, for example) based on the total weight of the drug-loaded microbead composition, may lead to decomposition or hydrolysis of the therapeutic agent, instability or breaking apart of the water-swellable polymer, or a combination of these, within a few days or even a few hours, such that the composition cannot be used for embolization procedures, even if the drug-loaded microbead composition is rehydrated. It is believed that the shelf-life and long-term stability of compositions having water contents significantly greater than 1% by weight are not sufficiently long to ensure viability of the therapeutic agent over the time period from manufacture of the drug-loaded microbead composition to use of the composition in an embolization procedure. It is believed that selection of the water-swellable polymer material may correlate with the ability for water to be removed from the drug-loaded microbeads by lyophilization or other drying technique or combination of drying techniques in an amount sufficient to prevent decomposition of the therapeutic agent.

A very low water content of the drug-loaded microbead composition, as previously described may be attained by drying techniques that will be described in greater detail subsequently, with respect to methods for preparing the drug-loaded microbead compositions. In this regard, the drug-loaded microbead compositions may be dry or nearly dehydrated compositions of the microbeads containing the embedded therapeutic agent or the embedded complex of the therapeutic agent and the carrier. The drug-loaded microbead compositions may have a powder-like consistency. Accordingly, the drug-loaded microbead compositions may be made suitable for injection into a subject being treated by rehydrating the microbeads of the drug-loaded microbead compositions to form an embolization composition, as will be described in greater detail subsequently. Regardless, the drug-loaded microbead compositions may be provided in such a form that a physician needs to add only an aqueous solution such as water or physiologically buffered saline solution to the drug-loaded microbead composition to prepare the composition for use in an embolization procedure.

The microbeads of the drug-loaded microbead composition may have any shape common to microparticles formed from a hydrogel type water-swellable polymer material. For example, the microparticles may be spherical or substantially spherical, or may have an ovoid shape with oval-shaped or elliptical cross-sections about a longitudinal axis and circular cross-sections about an axis perpendicular to the longitudinal axis.

The drug-loaded microbead composition may include an amount of therapeutic agent per unit volume of microbeads in the composition that is chosen to have a desired therapeutic effect or activity, based on the intended use for the drug-loaded microbead composition and the particular therapeutic agent present in the individual microbeads.

The amount of therapeutic agent in the individual microbeads of the drug-loaded microbead composition can be adjusted through particular techniques involved during drug loading, such as loading time, loading temperature, or concentration of therapeutic agent in a loading solution, for example. The amount of therapeutic agent in the individual microbeads of the drug-loaded microbead composition can be adjusted also through synthetic techniques involved for synthesizing the microbeads themselves, such as through adjusting polymer molecular weights, degree of hydrogel crosslinking, polymer density, or polymer porosity of the water-swellable polymer material. For example, when doxorubicin is the therapeutic agent, the amount of drug loading in the drug-loaded microbeads can be adjusted with respect to the number of negative charges in the polymer backbone of the water-swellable polymer material. Similarly, when sorafenib is the therapeutic agent, the sorafenib may be embedded within polymeric micelles or liposomes that can be embedded within the microbead structure. The amount of therapeutic agent in the individual microbeads of the drug-loaded microbead composition can be adjusted also through choice of the carrier.

In example embodiments, the individual drug-loaded microbeads of the drug-loaded microbead composition include the water-swellable polymer material, the therapeutic agent, the carrier, and water. The individual drug-loaded microbeads of the drug-loaded microbead composition may include from about 30% by weight to about 70% by weight, or from about 35% by weight to about 65% by weight, or from about 40% to about 60% by weight, or about 45% by weight to about 55% by weight, or about 50% to about 70% by weight water-swellable polymer material, based on the total weight of the individual drug-loaded microbead. In example embodiments, the individual drug-loaded microbeads of the drug-loaded microbead composition may include from about 1% by weight to about 25% by weight, or from about 1% by weight to about 20% by weight, or from about 1% by weight to about 15% by weight, or from about 2% by weight to about 25% by weight, or from about 5% by weight to about 25% by weight, or from about 10% by weight to about 25% by weight therapeutic agent, based on the total weight of the individual drug-loaded microbead. In example embodiments, the individual drug-loaded microbeads of the drug-loaded microbead composition may include from about 1% by weight to about 40% by weight, or from about 1% by weight to about 30% by weight, or from about 1% by weight to about 25% by weight, or from about 1% by weight to about 20% by weight, or from about 5% by weight to about 40% by weight, or from about 10% by weight to about 40% by weight, or from about 20% by weight to about 40% by weight carrier, based on the total weight of the individual drug-loaded microbead. In example embodiments, the individual drug-loaded microbeads of the drug-loaded microbead composition according to embodiments may have a very low water content such as less than 1% by weight, or less than 0.5% by weight, or less than 0.1% by weight, or less than 0.05% (500 ppm) by weight, or less than 0.02% (200 ppm) by weight, or less than 0.01% (100 ppm) by weight, or less than 0.005 (50 ppm) by weight, or less than 0.002% (20 ppm) by weight, or less than 0.001% (10 ppm) by weight water, based on the total weight of the individual microbeads in the drug-loaded microbead composition.

Having described drug-loaded microbead compositions according to various embodiments, methods for preparing the drug-loaded microbead compositions will now be described.

In some embodiments, methods for preparing a drug-loaded microbead composition as described previously may include dissolving a carrier and a therapeutic agent in an aqueous solvent to form an initial mixture. Within the initial mixture, complexes may form between molecules of the carrier and molecules of the therapeutic agent. For example, a mixture of doxorubicin as a therapeutic agent with a dextran sulfate as a carrier may form complexes of doxorubicin and dextran sulfate.

The initial mixture including the complexes may then be combined with a first solvent composition to form a second mixture. The first solvent composition includes a solvent or a mixture of solvents, in the combination of which the therapeutic agent is less soluble than in the aqueous solvent. The second mixture may be a biphasic or a multiphasic mixture. Then, the second mixture is rapidly agitated or stirred. The rapid agitation or stirring causes particles of the complex to form in the second mixture. The second mixture may be stirred, for example, at a stirring speed from about 150 rpm to about 2000 rpm. The stirring may be continuous and may be carried out for an amount of time sufficient to form microbeads. For example, the stirring may be carried out continuously for a stirring time from about 1 hour to about 12 hours. If the second mixture is biphasic, the particles may form in the phase of the second mixture in which the therapeutic agent is less soluble or least soluble. Optionally, the particles of the complex may be isolated from the second mixture by any suitable technique such as filtration, for example.

The particles of the complex, either still in the second mixture or optionally after isolation from the second mixture, may then be combined with a hydrogel of a water-swellable polymer material to form a hydrogel mixture. The hydrogel mixture is then combined with a second solvent composition to form a synthesis mixture. The second solvent composition includes a solvent or a mixture of solvents, in the combination of which the therapeutic agent and/or the hydrogel is less soluble than in aqueous solvent.

The synthesis mixture is agitated or stirred rapidly to form drug-loaded microbeads in the synthesis mixture. The synthesis mixture may be stirred, for example, at a stirring speed from about 150 rpm to about 2000 rpm. The stirring may be continuous and may be carried out for an amount of time sufficient to form microbeads. For example, the stirring may be carried out continuously for a stirring time from about 1 hour to about 12 hours. The drug-loaded microbeads may form either as the water-swellable polymer cures around the complex of the therapeutic agent or as the complex of the therapeutic agent absorbs into the polymer matrix of the water-swellable polymer. The drug-loaded microbeads are then recovered from the synthesis mixture by any suitable separation technique such as filtration, for example.

The drug-loaded microbeads prepared according to the foregoing procedure may exhibit a core-shell structure, in which a polymer matrix shell encapsulates a particle core and the complex is disposed in the particle core. In the core-shell structure, the therapeutic agent is not chemically bonded to the water-swellable polymer material and the carrier may be chemically bonded to the water-swellable polymer material.

In other embodiments, methods for preparing a drug-loaded microbead composition as described previously may include dissolving a carrier and a therapeutic agent in an aqueous solvent to form an initial mixture. Within the initial mixture, complexes may form between molecules of the carrier and molecules of the therapeutic agent. For example, a mixture of doxorubicin as a therapeutic agent with a dextran sulfate as a carrier may form complexes of doxorubicin and dextran sulfate. Subsequently, the initial mixture may be combined with a hydrogel solution of a water-swellable polymer material to form a hydrogel mixture, without first forming particles of the complex as an intermediate step.

The hydrogel mixture is then combined with a second solvent composition to form a synthesis mixture. The second solvent composition includes a solvent or a mixture of solvents, in the combination of which the therapeutic agent and/or the hydrogel is less soluble than in aqueous solvent. The synthesis mixture is stirred rapidly for form drug-loaded microbeads in the synthesis mixture. The drug-loaded microbeads may form either as the water-swellable polymer cures in the presence of the complex of the therapeutic agent or as the complex of the therapeutic agent absorbs into the polymer matrix of the water-swellable polymer. The drug-loaded microbeads are then recovered from the synthesis mixture by any suitable separation technique such as filtration, for example. The drug-loaded microbeads prepared according to the foregoing procedure may exhibit an interpenetrating network structure, in which the water-swellable polymer material has a polymer matrix and the complexes of the therapeutic agent and the carrier are disposed within pore structures of the polymer matrix. In the interpenetrating network structure, the therapeutic agent may be chemically bonded to the carrier, and the complex of the therapeutic agent and the carrier may be dispersed within molecules of the water-swellable polymer.

The foregoing methods for preparing drug-loaded microbead compositions, regardless of whether the drug-loaded microbeads are prepared including the intermediate step of forming particles of the complexes of therapeutic agent and carrier or without the intermediate step, further include removing water from the drug-loaded microbeads to form a drug-loaded microbead composition having a water content of less than 1% by weight, based on the total weight of the drug-loaded microbead composition. In some embodiments, the removal of the water may include lyophilization or freeze drying, optionally followed by an additional drying step involving temperature variation (heating or cooling), flowing air, vacuum, or a combination of these. The drug-loaded microbeads may have an average synthesized volume when recovered from the synthesis mixture and an average final volume after the removing of water. The average final volume may range from about 10% to about 75% of the average synthesized volume such as, for example, about 10%, about 20%, about 30%, about 40%, about 50%, about 60%, about 70%, or about 75% of the average synthesized volume.

Lyophilization or freeze drying of the drug-loaded microbeads may be conducted according to any procedure commonly used for drying of particulate substances. For example, the drug-loaded microbeads may be placed in partially stoppered glass vials, which then are placed on a cooled, temperature-controlled shelf within a freeze dryer. The shelf temperature is reduced, and the sample is frozen to a uniform, defined temperature. After complete freezing, the pressure in the dryer may be decreased to a defined pressure to initiate primary drying. During the primary drying, water vapor is progressively removed from the frozen mass by sublimation while the shelf temperature is controlled at a constant, low temperature. Secondary drying may be initiated by increasing the shelf temperature and reducing the chamber pressure further so that water absorbed to the semi-dried mass can be removed until the residual water content decreases to the desired level.

Lyophilization or freeze drying of the drug-loaded microbeads may also be conducted by atmospheric pressure freeze drying by rapidly circulating very dry air over the frozen drug-loaded microbeads. The circulating dry gas provides improved heat and mass transfer from the frozen microbeads. Atmospheric spray drying processes may facilitate the formation of small-diameter microbeads as a free-flowing powder, while avoiding formation of a dried cake. The free-flowing powder, in turn, may facilitate rehydration of the drug-loaded microbead composition when an embolization composition is prepared.

The drug-loaded microbeads of the drug-loaded microbead compositions previously described, or prepared according to the foregoing methods, may exhibit physical or mechanical properties beneficial to their use, storage, transport, or subsequent rehydration to form an embolization composition.

For example, it has been described previously that in the drug-loaded microbead compositions and embolization compositions according to embodiments of this disclosure, the therapeutic agent in the microbeads is not chemically bonded to the water-swellable polymer. Without intent to be bound by theory, it is believed that the lack of chemical bonding directly between the therapeutic agent and the water-swellable polymer causes microbeads of the water-swellable polymer to have substantially identical swollen diameters when loaded with therapeutic agent and when not loaded with therapeutic agent, whether before therapeutic agent is loaded into the microbeads or after therapeutic agent is eluted out of the microbeads.

In contrast, it has been observed that, some hydrogel polymer microbeads not according to embodiments of this disclosure have, in their swollen state without drug loading, an original diameter that shrinks by as much as 5% or 10% when drug is loaded into the polymer matrix of the microbeads. Without intent to be bound by theory, it is believed that such shrinkage results because the addition of drug molecules to the microbeads causes chemical bonds between the drug and the microbead polymer that, in turn, limit the amount of water that can be present in the microbead polymer to swell the microbead polymer.

In clinical practice, the shrinkage observed in some hydrogel polymer microbeads not according to embodiments of this disclosure is reversed when such a microbead composition is prepared for injection into a patient, because some amount of drug elutes out of the microbeads during the preparation process. Reversal of the shrinkage is exhibited as an increase in the diameters of the microbeads, even though drug is being removed or eluted. The diameters of such may become sufficiently large to clog a microcatheter being used to inject the microbeads. It is believed that the observed issues of microcatheter clogging are avoided through the drug-loaded microbead compositions and embolization compositions according to embodiments of this disclosure, in which the therapeutic agent is not chemically bonded to the water-swellable polymer material.

As a further illustration, mechanical properties of the drug-loaded microbeads may be tailored by adjusting properties of, or synthetic methods for, the water-swellable polymer material. For example, compression strength of the drug-loaded microbeads may be adjusted by changing the crosslinking agents used to prepare the microbeads or by changing the density or molecular weight of the water-swellable polymer materials through polymer synthesis techniques known and understood by those skilled in the art of polymer synthesis. In some embodiments, the drug-loaded microbeads of the drug-loaded microbead compositions may have physical and mechanical properties chosen, such that the drug-loaded microbeads recover greater than 85% of their diameter after being compressed to 50% of their initial diameter.

The drug-loaded microbeads of the drug-loaded microbead compositions previously described, or prepared according to the foregoing methods, may be provided to a physician with instructions for rehydrating the drug-loaded microbead composition to form an embolization composition that is ready for use in an embolization treatment. Accordingly, embodiments of this disclosure include embolization compositions and methods for preparing the embolization compositions.

An embolization composition may include a drug-loaded microbead composition according to any embodiment of this disclosure or a drug-loaded microbead composition prepared according to an embodied method of this disclosure. The embolization composition may further include amount of an aqueous solution sufficient to cause the drug-loaded microbeads of the drug-loaded microbead composition to swell. In particular, the amount of aqueous solution may cause the drug-loaded microbeads, after swelling, to have a water content of from about 50% by weight to about 99% by weight, from about 60% by weight to about 95% by weight, from about 70% by weight to about 95% by weight, from about 80% by weight to about 95% by weight, from about 90% by weight to about 95% by weight, or from about 80% by weight to about 99% by weight, or from about 90% by weight to about 99% by weight, or from about 95% by weight to about 99% by weight, based on the total weight of the drug-loaded microbeads. The aqueous solution may be any pharmaceutically acceptable solution such as, for, example, a physiologically buffered saline solution.

In example embodiments, the swollen individual drug-loaded microbeads of the embolization composition include the water-swellable polymer material, the therapeutic agent, the carrier, and water. The swollen individual drug-loaded microbeads of the embolization composition may include from about 3% by weight to about 10% by weight, from about 3% by weight to about 7% by weight, or from about 3.5% by weight to about 6.5% by weight, or from about 4% to about 6% by weight, or about 4.5% by weight to about 5.5% by weight, or about 5% to about 7% by weight water-swellable polymer material, based on the total weight of the swollen individual drug-loaded microbead. In example embodiments, the swollen individual drug-loaded microbeads of the embolization composition may include from about 0.1% by weight to about 2.5% by weight, or from about 0.1% by weight to about 2% by weight, or from about 0.1% by weight to about 1.5% by weight, or from about 0.2% by weight to about 2.5% by weight, or from about 0.5% by weight to about 2.5% by weight, or from about 1% by weight to about 2.5% by weight therapeutic agent, based on the total weight of the swollen individual drug-loaded microbead. In example embodiments, the swollen individual drug-loaded microbeads of the embolization composition may include from about 0.1% by weight to about 4% by weight, or from about 0.1% by weight to about 3% by weight, or from about 0.1% by weight to about 2.5% by weight, or from about 0.1% by weight to about 2% by weight, or from about 0.5% by weight to about 4% by weight, or from about 1% by weight to about 4% by weight, or from about 2% by weight to about 4% by weight carrier, based on the total weight of the swollen individual drug-loaded microbead. In example embodiments, the swollen individual drug-loaded microbeads of the embolization composition according to embodiments may have a water content of from about 50% by weight to about 99% by weight, from about 50% by weight to about 97% by weight, from about 50% by weight to about 96% by weight, from about 60% by weight to about 95% by weight, from about 70% by weight to about 95% by weight, from about 80% by weight to about 95% by weight, from about 90% by weight to about 95% by weight, or from about 80% by weight to about 99% by weight, or from about 90% by weight to about 99% by weight, or from about 95% by weight to about 99% by weight, based on the total weight of the individual drug-loaded microbeads.

The swollen microbeads of the embolization composition may have average diameters from about 5 μm to about 1200 μm, as measured by dynamic light scattering (DLS). For non-spherical microbeads, the diameter of an individual particle is taken to be the widest measurement attainable from a first point on the surface of the microbead, through the center of mass of the microbead, to a second point on the surface of the microbead opposite the first point. The specific size distribution of the microparticles may be chosen or tailored to suit the particular treatment for which the embolization composition is intended to be used. The average diameters of the microbeads in the embolization composition may be chosen by any suitable method of size selection before or after the therapeutic agent is loaded into the microbeads. In some embodiments, the swollen microbeads of the embolization composition may have average diameters such as, for example, from about 40 μm to about 800 μm, from about 40 μm to about 100 μm, from about 40 μm to about 75 μm, from about 75 μm to about 100 μm, from about 100 μm to about 200 μm, from about 200 μm to about 300 μm, from about 300 μm to about 400 μm, from about 400 μm to about 500 μm, from about 600 μm to about 700 μm, or any subset of any of the foregoing ranges. In some embodiments, the swollen microbeads may have average diameters with a narrow size distribution such as 40 μm±20 μm, or 40 μm±10 μm, or 40 μm±5 μm, or 40 μm±1 μm, for example.

Methods for preparing an embolization composition may include adding a drug-loaded microbead composition according to any embodiment of this disclosure, or a drug-loaded microbead composition prepared according to an embodied method of this disclosure, to an amount of an aqueous solution sufficient to cause the drug-loaded microbeads of the drug-loaded microbead composition to swell, whereby the drug-loaded microbeads after swelling comprise a water content of from 50% to 99% by weight, from 50% to 90% by weight, from 50% to 75% by weight, from 60% to 99% by weight, from 75% to 99% by weight, from 75% to 95% by weight, from 75% to 90% by weight, or from 85% to 99% by weight, based on the total weight of the drug-loaded microbeads, to form an injection-ready solution. The aqueous solution may be any pharmaceutically acceptable solution such as, for example, a physiologically buffered saline solution. The methods may further include loading the injection-ready solution into an injection device such as a syringe, for example. The methods may further include allowing the drug-loaded microbeads to swell for a rehydration time of from about 5 minutes to about 60 minutes before loading the injection-ready solution into the injection device. In some examples, the embolization composition may contain from about 25 mg therapeutic agent per milliliter of microbeads to about 150 mg therapeutic agent per milliliter of microbeads.

The embolization compositions prepared from the drug-loaded microbead compositions according to embodiments of this disclosure may be incorporated into an embolization treatment or therapy intended to treat a disease such as a cancer. In some embodiments, the therapeutic agent may be a chemotherapeutic agent having at least some efficacy for treating a cancer such as hepatocellular carcinoma, liver cancer, prostate cancer, or breast cancer. Accordingly, embodiments of this disclosure include methods for treating a disease. Methods for treating a disease may include providing intravenously, to a subject in need of embolization therapy, an embolization composition according to any embodiment previously described herein, prepared from a drug-loaded microbead composition according to any embodiment previously described herein.

In the methods for treating a disease, after the embolization composition is provided intravenously, at least a portion of the drug-loaded microbeads flow through vasculature of the subject to an embolization site and restrict blood flow through the embolization site. Thereafter, the drug-loaded microbeads may release to tissue at the embolization site over the course of a release period at least 90% by weight of the therapeutic agent, based on an initial amount of therapeutic agent embedded within the microbeads before the embolization composition is provided. In some embodiments, the release to the tissue at the embolization site may include an initial burst of drug release, during which at least 10% by weight of the therapeutic agent initially present in the drug-loaded microbeads is released into surrounding tissues at the embolization site. The initial burst may occur within 1 minute, 5 minutes, 10 minutes, 30 minutes, 60 minutes, 120 minutes, 180 minutes, 240 minutes, 300 minutes, 360 minutes, 12 hours, 18 hours, or 24 hours after the drug-loaded microbeads reach the embolization site. In some embodiments, the drug-loaded microbeads provide a sustained release of the therapeutic agent to the tissue over the release period. The release period may be an extended release period such as at least 5 days, at least 10 days, at least 14 days, at least 28 days, or at least 42 days. The end of release period is determined from the time when the drug-loaded microbeads are either completely decomposed or stop eluting therapeutic agent to the tissue.

Without intent to be bound by theory, it is believed that the release mechanism of the therapeutic agent from the drug-loaded microbeads of the embolization composition may be based on a dual mechanism including an ion exchange process and an enzymatic process. For example, it is believed that in an early stage of delivery of therapeutic agent to the embolization site, when plenty of water is present, the therapeutic agent may be released from the drug-loaded microbeads by ion exchange process. In a later stage, when water is lacking due to the vessel's being embolized, the drug-loaded microbeads may be degraded by an enzymatic process such as by lysozymes, for example, to release the therapeutic agent from the microbeads. It is believed that in the latest stage, such as by day 21 following implantation, most of the water-swellable polymer material has been resorbed through tissue surrounding the embolization site. Because at this point the water-swellable material no longer has a matrix encapsulating the therapeutic agent or the complex of the therapeutic agent and the carrier, the therapeutic agent can be completely eluted into the embolization site. Thereby, it is believed that the embolization compositions according to embodiments of this disclosure may increase tumor response and free survival rates. Additionally, the embolization compositions according to embodiments of this disclosure provide an economic value such as reducing the physician procedure time by eliminating a need to request a pharmacist or technician to add therapeutic agent to unloaded microbeads.

Reference will now be made in detail to embodiments of drug-loaded microbead compositions including microbeads or a biodegradable material loaded with at least two therapeutic agents. The microbead compositions according to embodiments include individual microbeads that contain a plurality of individual vesicular agents such as liposomes or ethosomes. At least one of the therapeutic agents is contained within the liposomes or ethosomes, either incorporated within a lipid bilayer or surrounded by a lipid bilayer. Another of the therapeutic agents may be contained within the individual vesicular agents or may be incorporated within a matrix formed by the biodegradable material of the microbeads but outside the individual vesicular agents. Further embodiments of this disclosure are directed to methods for preparing the drug-loaded microbead compositions, to embolization compositions prepared from the drug-loaded microbead compositions, to methods for preparing the embolization compositions, and to methods for treating a disease using the embolization compositions. The drug-loaded microbead compositions include microbeads into which a therapeutic agent has been pre-loaded. When included in an embolization composition and provided to a subject as part of an embolization therapy, the embolization compositions may provide a continuous release of the drug into the target treatment site for at least 7 days, at least 14 days, at least 21 days, or at least 30 days after implantation.

According to embodiments, drug-loaded microbead compositions include plurality of individual microbeads of a biodegradable material, a plurality of individual vesicular agents, a first therapeutic agent, and a second therapeutic agent different from the first therapeutic agent. In some embodiments, the plurality of individual vesicular agents may be contained within the individual microbeads, such as within pores of the individual microbeads. In some embodiments, the plurality of individual vesicular agents may be associated with the biodegradable material of the individual microbeads through ionic or non-covalent interaction, either entirely encompassed with a matrix of the biodegradable material or attached to the biodegradable material such as on an outer surface of the individual microbeads, for example. The vesicular agents include at least one lipid bilayer surrounding a vesicular core. The first therapeutic agent is associated with the individual vesicular agents. For example, the first therapeutic agent may be contained within the individual vesicular agents or may be associated with the individual vesicular agents by ionic or non-covalent interaction. The second therapeutic agent is different from the first therapeutic agent and is contained within the individual microbeads or associated with the individual microbeads through ionic or non-covalent interaction.

With respect to the vesicular agents and the therapeutic agents, the term "associated with" includes non-covalent interactions such as ionic bonds, van der Waals interactions, hydrogen bonding, pi-pi stacking, dipole-dipole interactions, dipole-quadrupole interactions, quadrupole-quadrupole interactions, multipole-multipole interactions, or combinations thereof. Ionic interactions or ionic bonding include a type of chemical bonding that involves the electrostatic attraction between oppositely charged ions such as anions or cations. In some examples, a therapeutic agent may include atoms or groups capable of forming ions or may have one or more natural dipoles. In such examples, the ions or dipoles may have particular affinity toward an oppositely charged ion or dipole naturally present in the vesicular agent or the biodegradable material. This affinity, in turn, results in a reversible chemical attraction or combination between the therapeutic agent and the vesicular agent or the biodegradable material.

The individual microbeads of the drug-loaded microbead compositions are microbeads of a biodegradable material. The biodegradable material or the individual microbeads forms a bead matrix that may include pores and may have various shapes or sizes. In some embodiments, the microbeads are spherical or ovoid. In some embodiments, the biodegradable material is a biodegradable polymer or a lipid. Examples of biodegradable polymers include, without limitation, poly(lactide-co-glycolide) (PLGA), polylactide (PLA), polyglycolide (PGA), polycaprolactone (PCL), polyhydroxyalkanoates, poly-R-3-hydroxybutyrate (poly3HB), poly-R-3-hydroxy-butyrate-co-R-3-hydroxyvalerate (poly (3HB-co-3HV)), poly-R-3-hydroxybutyrate-co-4-hydroxybutyrate (poly(3HB-co-4HB)), poly-R-3-hydroxyoctanoate-co-R-3-hydroxy-hexanoate (poly(3HO-co-3HH)), poly-3-hydroxypropionate (poly(3HP)), poly-4-hydroxy-butyrate (poly(4HB)), poly-5-hydroxybutyrate (poly(5HB)), poly-6-hydroxy-butyrate (poly(6HB)), poly(propylene fumarate), poly(butylene succinate), poly(p-dioxanone, polyacetals, poly(ortho esters), polycarbonates, chitosan, hydroxybutyric acids, polyanhydrides and polyesters, polyphosphazenes, polyphosphoesters, lipodisq, celluloses, modified celluloses, proteins and poly(amino acids), polyethers, and co-polymers of the foregoing. Examples of lipids include, without limitation, tricaprin, trilaurin, trimyristin, tripalmitin, tristearin, hydrogenated coco-glycerides, glyceryl monostearate, glyceryl behenate, glyceryl palmitostearate, glyceryl caprate, cetyl palmitate, stearic acid, palmitic acid, decanoic acid, behenic acid, beeswax, carnauba wax, cacao butter, and combinations thereof. In example embodiments, the drug-loaded microbead compositions include individual microbeads are beads of a biodegradable cellulose or a biodegradable modified cellulose such as cellulose acetate butyrate.

The biodegradable polymer materials of the drug-loaded microbead composition may include derivatives of any of the foregoing materials, or may include combinations of any of the foregoing materials or their derivatives. For example, the drug-loaded microbead compositions may include a combination of multiple biodegradable polymer materials, in which each individual microbead is made of a single type of polymer, and the drug-loaded microbead composition includes microbeads of multiple polymer types. Alternatively, the drug-loaded microbead compositions may include a combination of multiple biodegradable polymer materials, in which individual microbeads of the composition are composed of multiple types of polymer.

In various embodiments, the biodegradable material of the drug-loaded microbead composition may include a solid lipid such as tricaprin, trilaurin, trimyristin, tripalmitin, tristearin, hydrogenated coco-glycerides, glyceryl monostearate, glyceryl behenate, glyceryl palmitostearate, glyceryl caprate, cetyl palmitate, stearic acid, palmitic acid, decanoic acid, behenic acid, beeswax, carnauba wax, and cacao butter. The biodegradable materials of the drug-loaded microbead composition may include derivatives of any of the foregoing solid lipids, or may include combinations of any of the foregoing solid lipids or their derivatives. For example, the drug-loaded microbead compositions may include a combination of multiple solid lipids, in which each individual microbead is made of a single type of solid lipid, and the drug-loaded microbead composition includes microbeads of multiple solid lipids. Alternatively, the drug-loaded microbead compositions may include a combination of multiple solid lipids, in which individual microbeads of the composition are composed of multiple types of solid lipids.

In the drug-loaded microbead compositions according to embodiments, examples of vesicular agents include liposomes and ethosomes. Liposomes and ethosomes are particles having at least one amphipathic, spherical or nearly spherical bilayer formed by van der Waals interactions between a plurality of hydrophobic moieties each capped by a polar head group and arranged in an alternating manner such that a polar head group of one hydrophobic moiety projects outwardly to an external aqueous environment, while an adjacent hydrophobic moiety projects its polar head group inwardly. Liposomes can be classified according to their lamellarity (uni- and multilamellar vesicles), size (small, intermediate, or large), and charge (anionic, cationic and neutral) of the polar head groups. Liposome particles typically have diameters from about 0.025 µm to about 2.5 µm, in which the hydrophobic moieties are linear or lightly branched saturated hydrocarbons. Ethosomes are distinguished from liposomes in that the vesicular core of ethosomes includes aqueous ethanol solution. In embodiments, a therapeutic agent may be dissolved within the aqueous ethanol solution of ethosomes.

The vesicular agents such as liposomes or ethosomes, for example, include at least one lipid bilayer. The lipid bilayer may include a phospholipid. Examples of phospholipids include, without limitation, poly(2-methacryloyloxyethyl phosphorylcholine) (PMPC), soybean phosphatidylcholine (SW), hydrogenated soybean phosphatidylcholine (HSPC), egg sphingomyelin (ESM), egg phosphatidylcholine (EPC), dimyristoyl phosphatidylcholine (DMPC), dipalmitoyl phosphatidylcholine (DPPC), dioleoyl phosphatidylcholine (DOPC), distearoyl phosphatidylcholine (DSPC), dimyristoyl phosphatidylglycerol (DMPG), dipalmitoyl phosphatidylglycerol (DPPG), dioleoyl phosphatidylglycerol (DOPG), distearoyl phosphatidylglycerol (DSPC), dimyristoyl phosphatidylethanolamine (DMPE), dipalmitoyl phosphatidylethanolamine (DPPE), dioleoyl phosphatidylethanolamine (DOPE), dimyristoyl phosphatidylserine (LAMPS), dipalmitoyl phosphatidylserine (DPPS), dioleoyl phosphatidylserine (LOPS), 1,2-dioleoyl-3-trimethylammonium-propane (DOTAP), 1,2-dilauroyl-sn-glycero-3-phosphocholine (DLPC), 1,2-dimyristoyl-sn-glycero-3-phosphocholine (DMPC), 1,2-dimyristoyl-sn-glycero-3-phosphate (sodium salt) (DMPA.Na), 1,2-dipalmitoyl-sn-glycero-3-phosphate (sodium salt) (DPPA.Na), 1,2-dioleoyl-sn-glycero-3-phosphate (sodium salt) (DOPA.Na), 1,2-dimyristoyl-sn-glycero-3-phospho-(1'-rac-glycerol) (sodium salt) (DMPG.Na), 1,2-dipalmitoyl-sn-glycero-3-phospho-(1'-rac-glycerol) (sodium salt) (DPPG.Na), 1,2-dioleoyl-sn-glycero-3-phospho-(1'-rac-glycerol) (sodium salt) (DOPG.Na), 1,2-dimyristoyl-sn-glycero-3-phospho-L-serine (sodium salt) (DMPS.Na), 1,2-dipalmitoyl-sn-glycero-3-phospho-L-serine (sodium salt) (DPPS.Na), 1,2-dioleoyl-sn-glycero-3-phospho-L-serine (sodium salt) (DOPS.Na), 1,2-dioleoyl-sn-glycero-3-phosphoethanolamine-N-(glutaryl) (sodium salt) (DOPE-glutaryl (Na)$_2$), 1',3'-bis[1,2-dimyristoyl-sn-glycero-3-phospho]-sn-glycerol (ammonium salt) (Tetramyristoyl Cardiolipin 1,2-distearoyl-sn-glycero-3-phosphoethanolamine-N-[methoxy(polyethylene glycol)-2000] (ammonium salt) (DSPE-mPEG-2000, Na), 1,2-distearoyl-sn-glycero-3-phosphoethanolamine-N-[methoxy (polyethylene glycol)-5000] (ammonium salt) (DSPE-mPEG-5000.Na), 1,2-distearoyl-sn-glycero-3-phosphoethanolamine-N-[maleimide(polyethylene glycol)-2000] (ammonium salt) (DSPE-Maleimide PEG-2000.Na), 1,2-dioleoyl-3-trimethylammonium-propane (chloride salt) (DOTAP.Cl), 1,2-dihexanoyl-sn-glycero-3-phosphocholine (DHPC), and mixtures thereof, and salts thereof. In example embodiments, the lipid bilayer of the vesicle agents such as liposomes or ethosomes may be a combination of lipids. In a specific embodiment, the lipid bilayer of the vesicle agents such as liposomes or ethosomes may be a combination of poly(2-methacryloyloxyethyl phosphorylcholine) (PMPC), dioleoyl phosphatidylserine (DOPS), dioleoyl phosphatidylethanolamine (DOPE), and cholesterol.

The individual microbeads of the drug-loaded microbead compositions according to embodiments include at least two therapeutic agents, such as the first therapeutic agent and the second therapeutic agent. The first therapeutic agent is associated with or carried within the individual vesicular agents. For example, the first therapeutic agent may be contained within the individual vesicular agents or may be associated with the individual vesicular agents by ionic or non-covalent interaction. The first therapeutic agent may be within the lipid bilayer of the vesicular agents, within the vesicular core of the vesicular agents, or bound to the outer surface of the lipid bilayer and, therefore, not encapsulated by the vesicular agents.

The second therapeutic agent is different from the first therapeutic agent. The second therapeutic agent is contained within the individual microbeads or associated with the individual microbeads through ionic or non-covalent interaction. In some embodiments, the second therapeutic agent is contained within the individual vesicular agents of the individual microbeads or associated with individual vesicular agents through ionic or non-covalent interaction. For example, in some embodiments, the second therapeutic agent may be within the lipid bilayer of the vesicular agents, within the vesicular core of the vesicular agents, or bound to the outer surface of the lipid bilayer and, therefore, not encapsulated by the vesicular agents. In some embodiments, the second therapeutic agent is not contained within the individual vesicular agents and not ionically or non-covalently associated with the individual vesicular agents but, rather, is associated by ionic or non-covalent interaction with the biodegradable material of the individual microbeads. In such embodiments, the individual microbeads may contain vesicular agents loaded with the first therapeutic agent and molecules of the second therapeutic agent inside or attached to the matrix of biodegradable material that forms the individual microbeads but not inside the vesicular agents.

In some embodiments of the drug-loaded microbead composition the first therapeutic agent is hydrophobic and the second therapeutic agent is hydrophilic. In example embodiments, the first therapeutic agent may be encapsulated within the vesicular core of the individual vesicular agents and the second therapeutic agent may be contained within the lipid bilayer of the individual vesicular agents. In further example embodiments, the first therapeutic agent may be encapsulated within the vesicular core of the individual vesicular agents and the second therapeutic agent is not contained within the individual vesicular agents and is associated by ionic or non-covalent interaction with the biodegradable material of the individual microbeads.

The drug-loaded microbead compositions include at least two therapeutic agents. In embodiments, the first therapeutic agent and the second therapeutic agent are independently chosen from doxorubicin, bevacizumab, bortezomib, imatinib, seliciclib, ceritinib, everolimus, paclitaxel, sorafenib, irinotecan, idarubicin, cisplatin, pharmaceutically acceptable salts and derivatives thereof, and combinations thereof, provided the first therapeutic agent is different from the second therapeutic agent. In some embodiments, the therapeutic agent may be a hydrophilic therapeutic agent or a therapeutic agent that either is water soluble or has at least some solubility in an aqueous solution. In some embodiments, the therapeutic agent may be a chemotherapeutic agent having at least some efficacy for treating a disease such as cancer. In some embodiments, the therapeutic agent may be a chemotherapeutic agent having at least some efficacy for treating a cancer such as hepatocellular carcinoma, liver cancer, prostate cancer, or breast cancer. The therapeutic agent may have one or more chemical moieties or atomic centers having a positive or negative charge or affinity. Examples of specific therapeutic agents include, without limitation, doxorubicin, sorafenib, vandetanib, nivolumab, ipilimumab, regorafenib, irinotecan, epirubicin, pirarubicin, 5-fluorouracil, cisplatin, floxuridine, mitomycin C, derivatives of any of the foregoing, prodrugs of any of the foregoing, therapeutically acceptable salts or crystalline forms of any of the foregoing, or combinations of any of the foregoing. Further examples of suitable therapeutic agents include, without limitation, pirarubicin, mitoxantrone, tepotecan, paclitaxel, carboplatin, pemetrexed, penistatin, pertuzumab, trastuzumab, and docetaxel. Still further examples of suitable therapeutic agents include, without limitation, doxorubicin, bevacizumab, bortezomib, imatinib, seliciclib, ceritinib, everolimus, paclitaxel, sorafenib, irinotecan, idarubicin, cisplatin, and combinations of these drugs.

In an example embodiment of a drug-loaded microbead composition, the individual vesicular agents include liposomes; the first therapeutic agent is contained within the lipid bilayer of the individual vesicular agents; the second therapeutic agent is not contained within the individual vesicular agents and is associated by ionic or non-covalent interaction with the biodegradable material of the individual microbeads; and the biodegradable material is a cellulose. In such embodiments, the liposomes may include a lipid bilayer formed from a mixture of poly(2-methacryloyloxyethyl phosphorylcholine) (PMPC), dioleoyl phosphatidylserine (DOPS), dioleoyl phosphatidylethanolamine (DOPE), and cholesterol, for example.

In a further example embodiment of a drug-loaded microbead composition, the individual vesicular agents include liposomes; the first therapeutic agent is contained within the lipid bilayer of the individual vesicular agents; the second therapeutic agent is encapsulated within the vesicular core of the individual vesicular agents; the first therapeutic agent is sorafenib; the second therapeutic agent is doxorubicin; and the biodegradable material is a cellulose or modified cellulose such as ethyl cellulose or cellulose acetate butyrate. In such embodiments, the liposomes may include a lipid bilayer formed from a mixture of poly(2-methacryloyloxyethyl phosphorylcholine) (PMPC), dioleoyl phosphatidylserine (DOPS), dioleoyl phosphatidylethanolamine (DOPE), and cholesterol, for example.

In a further example embodiment of a drug-loaded microbead composition, the individual vesicular agents include ethosomes; the first therapeutic agent is encapsulated within the vesicular core of the individual vesicular agents; the second therapeutic agent is not contained within the individual vesicular agents and is associated by ionic or non-covalent interaction with the biodegradable material; the first therapeutic agent is sorafenib; the second therapeutic agent is doxorubicin; and the biodegradable material is a cellulose or modified cellulose such as ethyl cellulose or cellulose acetate butyrate. In such embodiments, the liposomes may include a lipid bilayer formed from a mixture of poly(2-methacryloyloxyethyl phosphorylcholine) (PMPC), dioleoyl phosphatidylserine (DOPS), dioleoyl phosphatidylethanolamine (DOPE), and cholesterol, for example.

In the individual microbeads of the drug-loaded microbead composition, the therapeutic agent or a complex of the therapeutic agent may be encapsulated by or embedded within the matrix formed by the biodegradable material. Except when described otherwise, the terms "encapsulated" and "embedded" broadly include embodiments for which the biodegradable material or some portion thereof generally surrounds the therapeutic agent and/or the vesicular agents including a therapeutic agent. For example, "embedded" may include in some embodiments a biodegradable material shell that encapsulates a core that holds the therapeutic agent and/or vesicular agents. In other embodiments, "embedded" may include a structure in which the therapeutic agent or the complex is physically disposed within a matrix, network, or pore structure of a biodegradable material that may or may not have a core within an outer shell. The therapeutic agent itself may not be chemically bonded to the biodegradable material at all or may not be chemically bonded directly to the polymer backbone of the biodegradable material when the biodegradable material is a biodegradable polymer material. The drug-loaded microbead composition may have a water content of less than 1% by weight, based on the total weight of the drug-loaded microbead composition.

In some embodiments, the therapeutic agent of the drug-loaded microbead composition may be embedded within the microbeads of the biodegradable material but not chemically bonded to the biodegradable material. In some embodiments, the therapeutic agent of the drug-loaded microbead composition may be embedded within the microbeads of the biodegradable material and not chemically bonded directly to a polymer backbone of the biodegradable material, yet may be chemically bonded to a functional group of the biodegradable material. As used herein, "not chemically bonded" refers to a lack of covalent chemical bonds between the therapeutic agent and the biodegradable but does not preclude the existence of noncovalent intermolecular interactions such as ionic interactions or a van der Waals interaction between the therapeutic agent and the biodegradable material.

In some embodiments, the vesicular agents form complexes of the therapeutic agent. In the complex, the therapeutic agent may be chemically bonded to the vesicular agents or the lipid bilayer thereof or may be associated with the vesicular agents or the lipid bilayer thereof by a non-covalent means such as encapsulation or a van der Waals interaction. The complex may be embedded within the biodegradable material. When the complex is embedded within the microbeads, the vesicular agents may be chemically bonded to the biodegradable material while the therapeutic agent is not chemically bonded to the biodegradable material. Without intent to be bound by theory, it is believed that when the therapeutic agent is bonded or associated with the vesicular agents but is not chemically bonded to the biodegradable material, the microbeads of the drug-loaded microbead composition are less susceptible to shrinking as a result of replacing water molecules with drug molecules during drug loading. Accordingly, the final size distribution of the drug-loaded microbeads can be controlled more readily by selecting appropriate microbead sizes before the therapeutic agent is loaded.

The drug-loaded microbead compositions according to embodiments may have a very low water content such as less than 1%, or less than 0.1%, or less than 0.05% (500 ppm), or less than 0.02% (200 ppm), or less than 0.01% (100 ppm), or less than 0.005 (50 ppm), or less than 0.002% (20 ppm), or less than 0.001% (10 ppm) by weight water, based on the total weight of the microbeads in the drug-loaded microbead composition. Without intent to be bound by theory, it is believed that a very low water content of the drug-loaded microbead composition increases the shelf-life and long-term stability of the drug-loaded microbead composition. Further, it is believed that water contents significantly greater than 1% by weight (such as 2%, 3%, 5%, or 10%, for example) based on the total weight of the drug-loaded microbead composition, may lead to decomposition or hydrolysis of the therapeutic agent, instability or breaking apart of the water-swellable polymer, or a combination of these, within a few days or even a few hours, such that the composition cannot be used for embolization procedures, even if the drug-loaded microbead composition is rehydrated. It is believed that the shelf-life and long-term stability of compositions having water contents significantly greater than 1% by weight are not sufficiently long to ensure viability of the therapeutic agent over the time period from manufacture of the drug-loaded microbead composition to use of the composition in an embolization procedure. It is believed that selection of the water-swellable polymer material may correlate with the ability for water to be removed from the drug-loaded microbeads by lyophilization or other drying technique or combination of drying techniques in an amount sufficient to prevent decomposition of the therapeutic agent.

A very low water content of the drug-loaded microbead composition, as previously described may be attained by drying techniques that will be described in greater detail subsequently, with respect to methods for preparing the drug-loaded microbead compositions. In this regard, the drug-loaded microbead compositions may be dry or nearly dehydrated compositions of the microbeads containing the embedded therapeutic agent or the embedded complex of the therapeutic agent and the vesicular agents. The drug-loaded microbead compositions may have a powder-like consistency. Accordingly, the drug-loaded microbead compositions may be made suitable for injection into a subject being treated by rehydrating the microbeads of the drug-loaded microbead compositions to form an embolization composition, as will be described in greater detail subsequently. Regardless, the drug-loaded microbead compositions may be provided in such a form that a physician needs to add only an aqueous solution such as water or physiologically buffered saline solution to the drug-loaded microbead composition to prepare the composition for use in an embolization procedure.

The microbeads of the drug-loaded microbead composition may have any shape common to microparticles formed from a hydrogel type water-swellable polymer material. For example, the microparticles may be spherical or substantially spherical, or may have an ovoid shape with oval-shaped or elliptical cross-sections about a longitudinal axis and circular cross-sections about an axis perpendicular to the longitudinal axis.

The drug-loaded microbead composition may include an amount of therapeutic agent per unit volume of microbeads in the composition that is chosen to have a desired therapeutic effect or activity, based on the intended use for the drug-loaded microbead composition and the particular therapeutic agent present in the individual microbeads.

The amount of therapeutic agent in the individual microbeads of the drug-loaded microbead composition can be adjusted through particular techniques involved during drug loading, such as loading time, loading temperature, or concentration of therapeutic agent in a loading solution, for example. The amount of therapeutic agent in the individual microbeads of the drug-loaded microbead composition can be adjusted also through synthetic techniques involved for synthesizing the microbeads themselves, such as through adjusting polymer molecular weights, polymer density, or polymer porosity of the biodegradable material. For example, when doxorubicin is the therapeutic agent, the amount of drug loading in the drug-loaded microbeads can be adjusted with respect to the number of negative charges in the polymer backbone of the water-swellable polymer material. Similarly, when sorafenib is the therapeutic agent, the sorafenib may be embedded within liposomes that are embedded within the microbead structure.

In example embodiments, the individual drug-loaded microbeads of the drug-loaded microbead composition include the biodegradable material, the first and second therapeutic agents, and water. The individual drug-loaded microbeads of the drug-loaded microbead composition may include from about 30% by weight to about 70% by weight, or from about 35% by weight to about 65% by weight, or from about 40% to about 60% by weight, or about 45% by weight to about 55% by weight, or about 50% to about 70% by weight biodegradable material, based on the total weight of the individual drug-loaded microbead. In example embodiments, the individual drug-loaded microbeads of the drug-loaded microbead composition may include from about 1% by weight to about 25% by weight, or from about 1% by weight to about 20% by weight, or from about 1% by weight to about 15% by weight, or from about 2% by weight to about 25% by weight, or from about 5% by weight to about 25% by weight, or from about 10% by weight to about 25% by weight therapeutic agent, based on the total weight of the individual drug-loaded microbead. In example embodiments, the individual drug-loaded microbeads of the drug-loaded microbead composition according to embodiments may have a very low water content such as less than 1% by weight, or less than 0.5% by weight, or less than 0.1% by weight, or less than 0.05% (500 ppm) by weight, or less than 0.02% (200 ppm) by weight, or less than 0.01% (100 ppm) by weight, or less than 0.005 (50 ppm) by weight, or less than 0.002% (20 ppm) by weight, or less than 0.001% (10 ppm) by weight water, based on the total weight of the individual microbeads in the drug-loaded microbead composition.

Having described drug-loaded microbead compositions according to various embodiments, methods for preparing the drug-loaded microbead compositions will now be described.

Example methods for preparing drug-loaded microbead compositions include preparing vesicular agents, adding the vesicular agents to an aqueous solution, preparing an organic solution containing a precursor to a biodegradable material, combining the aqueous solution and the organic solution, agitating the mixture to form microbeads, drying the microbeads, and recovering the microbeads. The methods may further include washing, rinsing, or filtering the microbeads.

The foregoing methods for preparing drug-loaded microbead compositions, regardless of whether the drug-loaded microbeads are prepared including the intermediate step of forming particles of the complexes of therapeutic agent and vesicular agents or without the intermediate step, further include removing water from the drug-loaded microbeads to form a drug-loaded microbead composition having a water content of less than 1% by weight, based on the total weight of the drug-loaded microbead composition. In some embodiments, the removal of the water may include lyophilization or freeze drying, optionally followed by an additional drying step involving temperature variation (heating or cooling), flowing air, vacuum, or a combination of these. The drug-loaded microbeads may have an average synthesized volume upon initial recovery and an average final volume after the removing of water. The average final volume may range from about 10% to about 75% of the average synthesized volume such as, for example, about 10%, about 20%, about 30%, about 40%, about 50%, about 60%, about 70%, or about 75% of the average synthesized volume.

Lyophilization or freeze drying of the drug-loaded microbeads may be conducted according to any procedure commonly used for drying of particulate substances. For example, the drug-loaded microbeads may be placed in partially stoppered glass vials, which then are placed on a cooled, temperature-controlled shelf within a freeze dryer. The shelf temperature is reduced, and the sample is frozen to a uniform, defined temperature. After complete freezing, the pressure in the dryer may be decreased to a defined pressure to initiate primary drying. During the primary drying, water vapor is progressively removed from the frozen mass by sublimation while the shelf temperature is controlled at a constant, low temperature. Secondary drying may be initiated by increasing the shelf temperature and reducing the chamber pressure further so that water absorbed to the semi-dried mass can be removed until the residual water content decreases to the desired level.

Lyophilization or freeze drying of the drug-loaded microbeads may also be conducted by atmospheric pressure freeze drying by rapidly circulating very dry air over the frozen drug-loaded microbeads. The circulating dry gas provides improved heat and mass transfer from the frozen microbeads. Atmospheric spray drying processes may facilitate the formation of small-diameter microbeads as a free-flowing powder, while avoiding formation of a dried cake. The free-flowing powder, in turn, may facilitate rehydration of the drug-loaded microbead composition when an embolization composition is prepared.

The drug-loaded microbeads of the drug-loaded microbead compositions previously described, or prepared according to the foregoing methods, may exhibit physical or mechanical properties beneficial to their use, storage, transport, or subsequent rehydration to form an embolization composition.

The drug-loaded microbeads of the drug-loaded microbead compositions previously described, or prepared according to the foregoing methods, may be provided to a physician with instructions for rehydrating the drug-loaded microbead composition to form an embolization composition that is ready for use in an embolization treatment. Accordingly, embodiments of this disclosure include embolization compositions and methods for preparing the embolization compositions.

An embolization composition may include a drug-loaded microbead composition according to any embodiment of this disclosure or a drug-loaded microbead composition prepared according to an embodied method of this disclosure. The embolization composition may further include amount of an aqueous solution sufficient to cause the drug-loaded microbeads of the drug-loaded microbead composition to reconstitute to a form suitable for administration to a patient. In particular, the amount of aqueous solution may cause the drug-loaded microbeads, after hydration, to have a water content of from about 50% by weight to about 99% by weight, from about 60% by weight to about 95% by weight, from about 70% by weight to about 95% by weight, from about 80% by weight to about 95% by weight, from about 90% by weight to about 95% by weight, or from about 80% by weight to about 99% by weight, or from about 90% by weight to about 99% by weight, or from about 95% by weight to about 99% by weight, based on the total weight of the drug-loaded microbeads. The aqueous solution may be any pharmaceutically acceptable solution such as, for, example, a physiologically buffered saline solution.

In example embodiments, the hydrated individual drug-loaded microbeads of the embolization composition include the biodegradable material, the therapeutic agent, the vesicular agents, and water. The hydrated individual drug-loaded microbeads of the embolization composition may include from about 3% by weight to about 10% by weight, from about 3% by weight to about 7% by weight, or from about 3.5% by weight to about 6.5% by weight, or from about 4% to about 6% by weight, or about 4.5% by weight to about 5.5% by weight, or about 5% to about 7% by weight biodegradable material, based on the total weight of the hydrated individual drug-loaded microbead. In example embodiments, the hydrated individual drug-loaded microbeads of the embolization composition may include from about 0.1% by weight to about 2.5% by weight, or from about 0.1% by weight to about 2% by weight, or from about 0.1% by weight to about 1.5% by weight, or from about 0.2% by weight to about 2.5% by weight, or from about 0.5% by weight to about 2.5% by weight, or from about 1% by weight to about 2.5% by weight therapeutic agent, based on the total weight of the hydrated individual drug-loaded microbead. In example embodiments, the hydrated individual drug-loaded microbeads of the embolization composition according to embodiments may have a water content of from about 50% by weight to about 99% by weight, from about 50% by weight to about 97% by weight, from about 50% by weight to about 96% by weight, from about 60% by weight to about 95% by weight, from about 70% by weight to about 95% by weight, from about 80% by weight to about 95% by weight, from about 90% by weight to about 95% by weight, or from about 80% by weight to about 99% by weight, or from about 90% by weight to about 99% by weight, or from about 95% by weight to about 99% by weight, based on the total weight of the individual drug-loaded microbeads.

The microbeads of the embolization composition may have average diameters from about 5 µm to about 1200 µm, as measured by dynamic light scattering (DLS). For non-spherical microbeads, the diameter of an individual particle is taken to be the widest measurement attainable from a first point on the surface of the microbead, through the center of mass of the microbead, to a second point on the surface of the microbead opposite the first point. The specific size distribution of the microparticles may be chosen or tailored to suit the particular treatment for which the embolization composition is intended to be used. The average diameters of the microbeads in the embolization composition may be chosen by any suitable method of size selection before or after the therapeutic agent is loaded into the microbeads. In some embodiments, the swollen microbeads of the embolization composition may have average diameters such as, for example, from about 40 µm to about 800 µm, from about 40 µm to about 100 µm, from about 40 µm to about 75 µm, from about 75 µm to about 100 µm, from about 100 µm to about 200 µm, from about 200 µm to about 300 µm, from about 300 µm to about 400 µm, from about 400 µm to about 500 µm, from about 600 µm to about 700 µm, or any subset of any of the foregoing ranges. In some embodiments, the swollen microbeads may have average diameters with a narrow size distribution such as 40 µm±20 µm, or 40 µm±10 µm, or 40 µm±5 µm, or 40 µm±1 µm, for example.

Methods for preparing an embolization composition may include adding a drug-loaded microbead composition according to any embodiment of this disclosure, or a drug-loaded microbead composition prepared according to an embodied method of this disclosure, to an amount of an aqueous solution sufficient to cause the drug-loaded microbeads of the drug-loaded microbead composition to swell, whereby the drug-loaded microbeads after swelling comprise a water content of from 50% to 99% by weight, from 50% to 90% by weight, from 50% to 75% by weight, from 60% to 99% by weight, from 75% to 99% by weight, from 75% to 95% by weight, from 75% to 90% by weight, or from 85% to 99% by weight, based on the total weight of the drug-loaded microbeads, to form an injection-ready solution. The aqueous solution may be any pharmaceutically acceptable solution such as, for example, a physiologically buffered saline solution. The methods may further include loading the injection-ready solution into an injection device such as a syringe, for example. The methods may further include allowing the drug-loaded microbeads to swell for a rehydration time of from about 5 minutes to about 60 minutes before loading the injection-ready solution into the injection device. In some examples, the embolization composition may contain from about 25 mg therapeutic agent per milliliter of microbeads to about 150 mg therapeutic agent per milliliter of microbeads.

The embolization compositions prepared from the drug-loaded microbead compositions according to embodiments of this disclosure may be incorporated into an embolization treatment or therapy intended to treat a disease such as a cancer. In some embodiments, the therapeutic agent may be a chemotherapeutic agent having at least some efficacy for treating a cancer such as hepatocellular carcinoma, liver cancer, prostate cancer, or breast cancer. Accordingly, embodiments of this disclosure include methods for treating a disease. Methods for treating a disease may include providing intravenously, to a subject in need of embolization therapy, an embolization composition according to any embodiment previously described herein, prepared from a drug-loaded microbead composition according to any embodiment previously described herein.

In the methods for treating a disease, after the embolization composition is provided intravenously, at least a portion of the drug-loaded microbeads flow through vasculature of the subject to an embolization site and restrict blood flow through the embolization site. Thereafter, the drug-loaded microbeads may release to tissue at the embolization site over the course of a release period at least 90% by weight of the therapeutic agent, based on an initial amount of therapeutic agent embedded within the microbeads before the embolization composition is provided. In some embodiments, the release to the tissue at the embolization site may include an initial burst of drug release, during which at least 10% by weight of the therapeutic agent initially present in the drug-loaded microbeads is released into surrounding tissues at the embolization site. The initial burst may occur within 1 minute, 5 minutes, 10 minutes, 30 minutes, 60 minutes, 120 minutes, 180 minutes, 240 minutes, 300 minutes, 360 minutes, 12 hours, 18 hours, or 24 hours after the drug-loaded microbeads reach the embolization site. In some embodiments, the drug-loaded microbeads provide a sustained release of the therapeutic agent to the tissue over the release period. The release period may be an extended release period such as at least 5 days, at least 10 days, at least 14 days, at least 28 days, or at least 42 days. The end of release period is determined from the time when the drug-loaded microbeads are either completely decomposed or stop eluting therapeutic agent to the tissue.

Without intent to be bound by theory, it is believed that the release mechanism of the therapeutic agent from the drug-loaded microbeads of the embolization composition may be based on a dual mechanism including an ion exchange process and an enzymatic process. For example, it is believed that in an early stage of delivery of therapeutic agent to the embolization site, when plenty of water is present, the therapeutic agent may be released from the drug-loaded microbeads by ion exchange process. In a later stage, when water is lacking due to the vessel's being embolized, the drug-loaded microbeads may be degraded by an enzymatic process such as by lysozymes, for example, to release the therapeutic agent from the microbeads. It is believed that in the latest stage, such as by day 21 following implantation, most of the biodegradable material has been resorbed through tissue surrounding the embolization site. Because at this point the water-swellable material no longer has a matrix encapsulating the therapeutic agent or the complex of the therapeutic agent and the vesicular agents, the therapeutic agent can be completely eluted into the embolization site. Thereby, it is believed that the embolization compositions according to embodiments of this disclosure may increase tumor response and free survival rates. Additionally, the embolization compositions according to embodiments of this disclosure provide an economic value such as reducing the physician procedure time by eliminating a need to request a pharmacist or technician to add therapeutic agent to unloaded microbeads.

Further embodiments of this disclosure are directed to drug-loaded biodegradable microbead compositions. The drug-loaded biodegradable microbead compositions may include microbeads of a biodegradable material and at least one therapeutic agent embedded in a matrix of the biodegradable material, encapsulated by a matrix of the biodegradable material, disposed within a porous structure formed by the matrix of the biodegradable material, or ionically or non-covalently associated with a matrix of the biodegradable material. In such embodiments of drug-loaded biodegradable microbead compositions, the microbeads of the biodegradable material may contain, but need not necessarily contain, vesicular agents such as liposomes or ethosomes.

In the drug-loaded biodegradable microbead compositions, the biodegradable material is a biodegradable polymer or a lipid. Examples of biodegradable polymers include, without limitation, poly(lactide-co-glycolide) (PLGA), polylactide (PLA), polyglycolide (PGA), polycaprolactone (PCL), polyhydroxyalkanoates, poly-R-3-hydroxybutyrate (poly3HB), poly-R-3-hydroxybutyrate-co-R-3-hydroxyvalerate (poly(3HB-co-3HV)), poly-R-3-hydroxybutyrate-co-4-hydroxybutyrate (poly(3HB-co-4HB)), poly-R-3-hydroxyoctanoate-co-R-3-hydroxyhexanoate (poly(3HO-co-3HH)), poly-3-hydroxypropionate (poly(3HP)), poly-4-hydroxybutyrate (poly(4HB)), poly-5-hydroxybutyrate (poly(5HB)), poly-6-hydroxybutyrate (poly(6HB)), poly(propylene fumarate), poly(butylene succinate), poly(p-dioxanone, polyacetals, poly(ortho esters), polycarbonates, chitosan, hydroxybutyric acids, polyanhydrides and polyesters, polyphosphazenes, polyphosphoesters, lipodisq, celluloses, modified celluloses, proteins and poly(amino acids), polyethers, and co-polymers of the foregoing. Examples of lipids include, without limitation, tricaprin, trilaurin, trimyristin, tripalmitin, tristearin, hydrogenated coco-glycerides, glyceryl monostearate, glyceryl behenate, glyceryl palmitostearate, glyceryl caprate, cetyl palmitate, stearic acid, palmitic acid, decanoic acid, behenic acid, beeswax, carnauba wax, cacao butter, and combinations thereof. In example embodiments, the drug-loaded microbead compositions include individual microbeads are beads of a biodegradable cellulose or a biodegradable modified cellulose such as ethyl cellulose or cellulose acetate butyrate. The biodegradable polymer materials of the drug-loaded biodegradable microbead composition may include derivatives of any of the foregoing materials, or may include combinations of any of the foregoing materials or their derivatives. For example, the drug-loaded microbead compositions may include a combination of multiple biodegradable polymer materials, in which each individual microbead is made of a single type of polymer, and the drug-loaded biodegradable microbead composition includes microbeads of multiple polymer types. Alternatively, the drug-loaded biodegradable microbead compositions may include a combination of multiple biodegradable polymer materials, in which individual microbeads of the composition are composed of multiple types of polymer.

In various embodiments, the biodegradable material of the drug-loaded biodegradable microbead composition may include a solid lipid such as tricaprin, trilaurin, trimyristin, tripalmitin, tristearin, hydrogenated coco-glycerides, glyceryl monostearate, glyceryl behenate, glyceryl palmitostearate, glyceryl caprate, cetyl palmitate, stearic acid, palmitic acid, decanoic acid, behenic acid, beeswax, carnauba wax, and cacao butter. The biodegradable materials of the drug-loaded biodegradable microbead composition may include derivatives of any of the foregoing solid lipids, or may include combinations of any of the foregoing solid lipids or their derivatives. For example, the drug-loaded biodegradable microbead compositions may include a combination of multiple solid lipids, in which each individual microbead is made of a single type of solid lipid, and the drug-loaded biodegradable microbead composition includes microbeads of multiple solid lipids. Alternatively, the drug-loaded biodegradable microbead compositions may include a combination of multiple solid lipids, in which individual microbeads of the composition are composed of multiple types of solid lipids.

In the drug-loaded biodegradable microbead compositions, the at least one therapeutic agent may be chosen from doxorubicin, bevacizumab, bortezomib, imatinib, seliciclib, ceritinib, everolimus, paclitaxel, sorafenib, irinotecan, idarubicin, cisplatin, pharmaceutically acceptable salts and derivatives thereof, and combinations thereof. Further examples of specific therapeutic agents include, without limitation, doxorubicin, sorafenib, vandetanib, nivolumab, ipilimumab, regorafenib, irinotecan, epirubicin, pirarubicin, 5-fluorouracil, cisplatin, floxuridine, mitomycin C, derivatives of any of the foregoing, prodrugs of any of the foregoing, therapeutically acceptable salts or crystalline forms of any of the foregoing, or combinations of any of the foregoing. Further examples of suitable therapeutic agents include, without limitation, pirarubicin, mitoxantrone, tepotecan, paclitaxel, carboplatin, pemetrexed, penistatin, pertuzumab, trastuzumab, and docetaxel. Still further examples of suitable therapeutic agents include, without limitation, doxorubicin, bevacizumab, bortezomib, imatinib, seliciclib, ceritinib, everolimus, paclitaxel, sorafenib, irinotecan, idarubicin, cisplatin, and combinations of these drugs. In one specific embodiment of the drug-loaded biodegradable microbead compositions, the at least one therapeutic agent includes doxorubicin. In one specific embodiment of the drug-loaded biodegradable microbead compositions, the at least one therapeutic agent includes sorafenib. In one specific embodiment of the drug-loaded biodegradable microbead compositions, the at least one therapeutic agent includes paclitaxel. In some embodiments, the microbeads of the drug-loaded biodegradable microbead compositions include combinations of two, three, four, or greater than four therapeutic agents. In one specific embodiment of the drug-loaded biodegradable microbead compositions, the at least one therapeutic agent includes a combination of doxorubicin and sorafenib. In some embodiments, the biodegradable material and the at least one therapeutic agent are both hydrophobic, thereby facilitating homogeneous distribution of the therapeutic agent throughout the matrix of the biodegradable material.

The microbeads of the drug-loaded biodegradable microbead compositions may be prepared by any suitable process including, but not limited to, emulsion and microfluidics. Emulsion methods include preparing an aqueous phase of water and, optionally, an emulsifier such as polyvinyl alcohol; preparing an organic phase of a biodegradable material, a hydrophobic therapeutic agent, and a water-immiscible organic solvent; mixing the aqueous phase and the organic phase to form an emulsion; evaporating the solvents to dry the microbeads formed from the emulsion; recovering and further drying the microbeads; isolating desired size ranges of beads by filtering or sieving; optionally further drying and/or dehydrating and/or lyophilizing the microbeads; and sterilizing the microbeads. The microbeads may be rehydrated or reconstituted by adding a fluid such as water or physiologically buffered saline. Microbeads formed in this manned may have sizes from 20 µm to 900 µm, for example, and can be sieved to narrow ranges. The ratio of biodegradable material to therapeutic agent by weight may be from 100:1 to 0.01:1, or from 10:1 to 0.1:1, or any desired range between these ranges, for example. Microfluidics methods include similarly preparing aqueous and organic phases and, in a microfluidic apparatus, flowing small volumes of organic phase through the aqueous phase to produce small droplets in the aqueous phase that may be collected as microbeads at an exit of the apparatus.

Further embodiments of the present disclosure are directed to a drug-loaded microbead composition for use in a therapeutic embolization procedure. The drug-loaded microbead composition can be any of the drug-loaded microbead compositions that are described herein, and can be used in the form of an embolization composition according to any embodiment described herein. The therapeutic embolization procedure is preferably one for treating tumors. The therapeutic embolization procedure is preferably one for treating hepatocellular carcinoma, liver cancer, prostate cancer, or breast cancer.

EXAMPLES

The following examples are offered by way of illustration only. In view of the foregoing description, the person having ordinary skill in the art will recognize that the following examples are not intended to limit the scope of this disclosure or its many embodiments.

Example 1

A drug-loaded microbead composition of this Example includes polymer microbeads and a complex comprising a dextran sulfate chemically bonded to doxorubicin. The complex is encapsulated within a core of the microbead, defined within a shell of water-swellable polymer material. The microbeads have size ranges from 10 μm to 2000 μm. The drug-loaded microbead composition contains from about 25 mg doxorubicin per milliliter of microbeads to about 150 mg doxorubicin per milliliter of microbeads.

To prepare the drug-loaded microbead composition, a dextran-doxorubicin complex is prepared made by dissolving dextran sodium sulfate (molecular weight range 40 kDa to 500 kDa) and doxorubicin in an aqueous solution. Then the dextran-doxorubicin solution is added into a solvent mixture with high speed stirring to generate doxorubicin-loaded dextran particles. The doxorubicin-loaded particles are added into a hydrogel solution of the polymer material and are encapsulated within the microbead core by a water/oil process. In the water/oil process, the doxorubicin-loaded dextran particles are present in an aqueous solvent, to which additional solvents are added to create a biphasic mixture. The biphasic mixture includes an aqueous phase, in which the doxorubicin-loaded dextran particles are initially present with the hydrogel, and an oil phase. On rapid mixing of the biphasic mixture, the doxorubicin-loaded dextran particles are incorporated into microbeads of the hydrogel polymer within the oil phase of the biphasic mixture.

After being recovered from the biphasic mixture, the drug-loaded microbeads contain a substantial amount of water and are in a swollen state. To prepare the drug-loaded microbead composition for packaging, the microbeads are subjected to lyophilization to remove water. The lyophilization process removes greater than 90% by weight, or greater than 95% by weight, or greater than 98%, or greater than 99% by weight, or greater than 99.9% by weight, or greater than 99.99% by weight of the total water present in the microbeads immediately after the drug loading. The lyophilized microbeads may be subjected to further drying in air and/or vacuum. Thereby, the drug-loaded microbead composition contains less than 1%, or less than 0.1%, or less than 0.05% (500 ppm), or less than 0.02% (200 ppm), or less than 0.01% (100 ppm), or less than 0.005 (50 ppm), or less than 0.002% (20 ppm), or less than 0.001% (10 ppm) by weight water, based on the total weight of the drug-loaded microbead composition.

Example 2

A drug-loaded microbead composition of this Example also includes polymer microbeads and a complex comprising a dextran sulfate chemically bonded to doxorubicin. The complex is encapsulated within a core of the microbead, defined within a shell of water-swellable polymer material. The microbeads have size ranges from 10 μm to 2000 μm. The drug-loaded microbead composition contains from about 25 mg doxorubicin per milliliter of microbeads to about 150 mg doxorubicin per milliliter of microbeads.

To prepare the drug-loaded microbead composition, a dextran-doxorubicin complex is prepared made by dissolving dextran sodium sulfate (molecular weight range 40 kDa to 500 kDa) and doxorubicin in an aqueous solution. Unlike in Example 1, in which doxorubicin-loaded dextran particles are generated as an intermediate step, the dextran-doxorubicin solution is combined directly with a hydrogel solution of the polymer material to form a synthesis mixture. After vigorous mixing, drug-loaded microbeads form, in which the microbeads are embedded within an interpenetrating network of water-swellable polymer material and dextran, and the doxorubicin is complexed to the dextran without being chemically bonded to the water-swellable polymer material. The drug-loaded microbeads are recovered from the synthesis mixture.

After being recovered from the synthesis mixture, the drug-loaded microbeads contain a substantial amount of water and are in a swollen state. To prepare the drug-loaded microbead composition for packaging, the microbeads are subjected to lyophilization to remove water. The lyophilization process removes greater than 90% by weight, or greater than 95% by weight, or greater than 98%, or greater than 99% by weight, or greater than 99.9% by weight, or greater than 99.99% by weight of the total water present in the microbeads immediately after the drug loading. The lyophilized microbeads may be subjected to further drying in air and/or vacuum. Thereby, the drug-loaded microbead composition contains less than 1%, or less than 0.1%, or less than 0.05% (500 ppm), or less than 0.02% (200 ppm), or less than 0.01% (100 ppm), or less than 0.005 (50 ppm), or less than 0.002% (20 ppm), or less than 0.001% (10 ppm) by weight water, based on the total weight of the drug-loaded microbead composition.

Example 3

A drug-loaded microbead composition is prepared according to Example 1 or Example 2. The drug-loaded microbead composition is then mixed with physiologically buffered saline solution for a rehydration time of from 5 minutes to 40 minutes to swell the microbeads and form an embolization composition (A). The solution containing the swollen microbeads is then injected into a patient.

To compare the in vitro doxorubicin release rates of the drug-loaded microbead composition prepared according to Example 1 or Example 2 to those of other microbead compositions prepared from beads of non-degradable polymer materials, two comparative samples are prepared and injected into a patient. The first comparative sample (B) contains microbeads of biocompatible sulfonate-modified poly(vinyl alcohol) loaded with doxorubicin by adding the doxorubicin in an aqueous solution to the unloaded microbeads and waiting about 24 hours before injection. The second comparative sample (C) contains microbeads of a sodium acrylate alcohol copolymer formed by polymerization of vinyl acetate and methyl acrylate and loaded with doxorubicin by adding the doxorubicin in an aqueous solution to the unloaded microbeads and waiting about 24 hours before injection.

A comparison of the doxorubicin release rates of the three samples from injection until 30 days after injection is provided in the FIGURE. The embolization composition (A) prepared from the drug-loaded microbead composition of Example 1 or Example 2 exhibits an initial burst of doxorubicin release over the first two days, during which approximately 30% of the total doxorubicin content is released to the tissues of the patient. The doxorubicin release continues through day 14, by which time approximately 70% of the total doxorubicin content of the microbeads has been released, and further through day 30, by which time approximately 90% to 100% of the total doxorubicin content of the microbeads has been released.

In contrast, the first sample (B) releases approximately 20% of its doxorubicin immediately and by day 2 has released approximately 25% of its doxorubicin content. After day 2, however, no further doxorubicin is released. Similarly, the second comparative sample (C) releases approximately 15% of its doxorubicin immediately and does not release any additional doxorubicin after the initial release.

Example 4

Liposomes including sorafenib incorporated within a lipid bilayer are prepared by subjecting a mixture of 37 mol. % poly(2-methacryloyloxyethyl phosphorylcholine) (PMPC), 12 mol. % dioleoyl phosphatidyl-serine (DOPS), 12 mol. % dioleoyl phosphatidyl-ethanolamine (DOPE), 26 mol % cholesterol and 13 Mol % sorafenib in chloroform solvent to a centrifugation extrusion with a 200-nm polycarbonate membrane. The size of the liposomes, as determined by Dynamic Light Scattering (DLS), is 171.8±3.0 nm. Presence of sorafenib in the final liposome preparation is verified from an absorbance peak at about 270 nm, measured by UV-VIS spectroscopy.

Example 5

Liposomes including doxorubicin surrounded by a lipid bilayer are prepared by subjecting a mixture of PMPC, DOI'S, DOPE, and cholesterol in chloroform to a centrifugation extrusion with a 200-nm polycarbonate membrane. The chloroform solvent is dried from the mixture. The lipid mixture is then rehydrated with an aqueous solution of HEPES, salt, and doxorubicin, to form liposomes. Excess doxorubicin not incorporated within the liposomes is removed by gel filtration.

Example 6

Ethosomes including sorafenib surrounded by a lipid bilayer are prepared by centrifugation extrusion with a 200-nm polycarbonate membrane of a mixture of 42 mol. % PMPC, 14 mol. % DOPS, 14 mol. % DOPE, and 30 mol. % cholesterol in a 40% ethanol/water solution containing 2 mM sorafenib. Free sorafenib is separated from the ethosomes by size exclusion chromatography on Sephadex G-25. The sorafenib ethosomes have sizes 234.4±4.5 nm determined by dynamic light scattering. Presence of sorafenib in the final liposome preparation is verified from an absorbance peak at about 270 nm, measured by UV-VIS spectroscopy.

Example 7

Liposomes including sorafenib within a lipid bilayer and doxorubicin surrounded by the lipid are prepared by subjecting a mixture of 37 mol. % poly(2-methacryloyloxyethyl phosphorylcholine) (PMPC), 12 mol. % dioleoyl phosphatidyl-serine (DOPS), 12 mol. % dioleoyl phosphatidyl-ethanolamine (DOPE), 26 mol. % cholesterol and 13 mol. % sorafenib in chloroform solvent to a centrifugation extrusion with a 200-nm polycarbonate membrane. The solvent is dried from the lipid/sorafenib mixture. The lipid mixture is then rehydrated with an aqueous solution of HEPES, salt, and doxorubicin, to form liposomes. Excess doxorubicin not incorporated within the liposomes is removed by gel filtration.

Example 8

Vesicular agents such as the liposomes or ethosomes prepared according to any of Examples 4-7 are incorporated into microbeads of a biodegradable material by emulsion evaporation. An emulsion is prepared from an aqueous phase of deionized water and an emulsifier such as polyvinyl alcohol and an organic phase containing the vesicular agents and biodegradable polymer material.

An aqueous phase of 1% polyvinyl alcohol is prepared by stirring 8 g polyvinyl alcohol (86-89% hydrolyzed) into 800 mL deionized water at 600 rpm at 85° C. for 3-4 hours until the polyvinyl alcohol is fully dissolved.

An organic phase is prepared by adding to a 2-mL vial 150 mg cellulose acetate butyrate and 900 μL dichloromethane, sealing the vial, and shaking the vial until the cellulose acetate butyrate is dissolved. To the mixture, 100 μL of the vesicular agent in aqueous solution is added.

The organic phase and the aqueous phase are mixed by first adding to an appropriate vessel, such as a 250-mL flask, 100 mL of the aqueous phase then adding the contents of the vial of organic phase into the flask while stirring the aqueous phase in the flask at approximately 600 rpm. The flask is sealed with a lid, and stirring is continued for 30 minutes. After the thirty minutes, the lid is removed and the contents of the flask are stirred without the lid for an additional 2 hours. The stirring is then stopped, and the microbeads that have formed in the solution are allowed to settle.

The microbeads are then transferred by pipette to centrifuge tubes, and the tubes are centrifuged at 12000 rpm or greater for at least 2.5 minutes. The supernatant is then removed by transfer pipette, and the microbeads are washed by refilling the tubes a with deionized or filtered water and centrifuging again at 12000 rpm or greater for at least 2.5 minutes. The washing process is repeated from one to five times. The resulting microbeads have sizes from about 20 μm to about 350 μm.

The centrifuged microbeads are vacuum filtered through 200-micron mesh filters into a vacuum flask. The filtered microbeads in the flask have sizes from about 20 μm to about 200 The filtered microbeads in the flask are then further vacuum filtered through a 100-micron mesh filter. The microbeads remaining on the filter are retained and have sizes from about 100 μm to about 200 These microbeads are rinsed with filtered water then are allowed to dry in air for 24 hours. The air-dried microbeads then may be transferred to a suitable container or vial.

Items Listing

Embodiments of the present disclosure include at least following Items, which are not intended to limit the scope of the disclosure as a whole or the appended claims.

Item A1: A drug-loaded microbead composition comprising: microbeads comprising a water-swellable polymer material; and a complex comprising a carrier and a therapeutic agent chemically bonded to the carrier, wherein: the complex is embedded within the polymer material; and the drug-loaded microbead composition has a water content of less than 1% by weight, based on the total weight of the drug-loaded microbead composition.

Item A2: The drug-loaded microbead composition of Item A1, wherein the water-swellable polymer material is a biodegradable polymer material chosen from poly(-hydroxybutyrate), methacrylated hyaluronic acids, chitosan-alginate, poly(N-isopropylacrylamide) copolymers, poly(N-isopropylacrylamide)-alginates, poly(N-isopropylacrylamide)-peptides, poly(N-isopropylacrylamide)-α-acryloyloxy-β,β-dimethyl-γ-butyrolactone-hydrophilic Jeffamine, poly(N-isopropylacrylamide)-poly(ethylene glycol) diacrylate-pentaerythritol tetrakis(3-mercaptopropionate), derivatives of any of the foregoing, or combinations of any of the foregoing.

Item A3: The drug-loaded microbead composition of Item A1 or A2, wherein the therapeutic agent is chosen from doxorubicin, sorafenib, vandetanib, nivolumab, ipilimumab, regorafenib, irinotecan, epirubicin, pirarubicin, 5-fluorouracil, cisplatin, floxuridine, mitomycin C, derivatives of any of the foregoing, prodrugs of any of the foregoing, therapeutically acceptable salts of any of the foregoing, or combinations of any of the foregoing.

Item A4: The drug-loaded microbead composition of any one of the preceding Items, wherein the therapeutic agent is not chemically bonded to the water-swellable polymer material.

Item A5: The drug-loaded microbead composition of any one of the preceding Items, wherein: the water-swellable polymer material comprises a polymer matrix shell encapsulating a particle core; and the complex is disposed within the particle core.

Item A6: The drug-loaded microbead composition of any one of the preceding Items, wherein the carrier is embedded within an interpenetrating network of the water-swellable polymer material of the drug-loaded microbead.

Item A7: The drug-loaded microbead composition of any one of the preceding Items, wherein the carrier is chosen from liposomes, polymeric micelles, Pluronics, polycaprolactone-b-methoxy-PEG, poly(aspartic acid)-b-PEG, poly(benzyl-L-glutamate)-b-PEG, poly(D,L-lactide)-b-methoxy-PEG, poly($\beta$-benzyl-L-aspartate)-b-PEG), or sodium dextran sulfate.

Item A8: The drug-loaded microbead composition of Item A6, wherein the carrier comprises a sodium dextran sulfate.

Item A9: The drug-loaded microbead composition of Item A8, wherein the sodium dextran sulfate has a molecular weight of from about 40 kDa to about 500 kDa.

Item A10: The drug-loaded microbead composition of Item A7, wherein the carrier comprises liposomes.

Item A11: The drug-loaded microbead composition of Item A7, wherein the carrier comprises polymeric micelles.

Item A12: The drug-loaded microbead composition of Item A7, wherein the carrier comprises Pluronics.

Item A13: The drug-loaded microbead composition of Item A7, wherein the carrier comprises polycaprolactone-b-methoxy-PEG.

Item A14: The drug-loaded microbead composition of Item A7, wherein the carrier comprises poly(aspartic acid)-b-PEG.

Item A15: The drug-loaded microbead composition of Item A7, wherein the carrier comprises poly(benzyl-L-glutamate)-b-PEG.

Item A16: The drug-loaded microbead composition of Item A7, wherein the carrier comprises poly(D,L-lactide)-b-methoxy-PEG.

Item A17: The drug-loaded microbead composition of Item A7, wherein the carrier comprises poly($\beta$-benzyl-L-aspartate)-b-PEG).

Item A18: The drug-loaded microbead composition of any one of the preceding Items, wherein the drug-loaded microbeads are substantially spherical.

Item A19: The drug-loaded microbead composition of any one of the preceding Items, wherein the drug-loaded microbeads have diameters from about 40 µm to about 800 µm.

Item A20: The drug-loaded microbead composition of any one of the preceding Items, wherein individual microbeads of the drug loaded microbead composition comprise, based on the total weight of the individual microbeads: from about 30% by weight to about 70% by weight water-swellable polymer material; from about 1% by weight to about 25% by weight therapeutic agent; from about 1% by weight to about 40% by weight carrier; and less than 1% by weight water.

Item A21: A method for preparing a drug-loaded microbead composition, the method comprising: dissolving a carrier and a therapeutic agent in an aqueous solvent to form an initial mixture, the initial mixture comprising a complex of the carrier and the therapeutic agent; combining the initial mixture with a first solvent composition in which the therapeutic agent is less soluble than in the aqueous solvent to form a second mixture; stirring the second mixture rapidly to form particles of the complex in the second mixture; combining the particles of the complex with a hydrogel of a water-swellable polymer material to form a hydrogel mixture; combining the hydrogel mixture with a second solvent composition to form a synthesis mixture; stirring the synthesis mixture rapidly to form drug-loaded microbeads in the synthesis mixture; recovering the drug-loaded microbeads from the synthesis mixture; and removing water from the drug-loaded microbeads to form a drug-loaded microbead composition having a water content of less than 1% by weight, based on the total weight of the drug-loaded microbeads in the drug-loaded microbead composition.

Item A22: The method of Item A21, further comprising filtering the second mixture to recover the particles of the complex before combining the particles of the complex with the hydrogel solution.

Item A23: The method of Item A21 or A22, wherein the removing water comprises lyophilizing the drug-loaded microbeads.

Item A24: The method of Item A21 or A22, wherein: the removing water comprises lyophilizing the drug-loaded microbeads; and drying the lyophilized drug-loaded microbeads by air, temperature variation, vacuum, or any combination thereof.

Item A25: The method of any one of Items A21-A24, wherein: the drug-loaded microbeads have an average synthesized volume when recovered from the synthesis mixture and an average final volume after the removing of water; and the average final volume is from about 10% to about 75% of the average synthesized volume.

Item A26: A method for preparing a drug-loaded microbead composition, the method comprising: dissolving a carrier and a therapeutic agent in an aqueous solvent to form an initial mixture, the initial mixture comprising a complex of the carrier and the therapeutic agent; combining the initial mixture with a hydrogel solution of a water-swellable polymer material to form a hydrogel mixture; combining the hydrogel mixture with a solvent composition to form a synthesis mixture; stirring the synthesis mixture rapidly to form drug-loaded microbeads in the synthesis mixture; recovering the drug-loaded microbeads from the synthesis mixture; and drying the drug-loaded microbeads to form a drug-loaded microbead composition having a water content of less than 1% by weight, based on the total weight of the drug-loaded microbeads in the drug-loaded microbead composition.

Item A27: The method of Item A26, wherein the removing water comprises lyophilizing the drug-loaded microbeads.

Item A28: The method of Item A26, wherein: the removing water comprises lyophilizing the drug-loaded microbeads; and drying the lyophilized drug-loaded microbeads in air, heat, vacuum, or any combination thereof.

Item A29: The method of any one of Items A26-A28, wherein the drug-loaded microbeads have an average synthesized volume when recovered from the synthesis mixture and an average final volume after the removing of water; and the average final volume is from about 10% to about 75% of the average synthesized volume.

Item A30: An embolization composition comprising: a drug-loaded microbead composition according to any of Items A1-A20, or a drug-loaded microbead composition made by the method according to any of Items A21-A25, or a drug-loaded microbead composition made by the method according to any of Items A26-A29; and an amount of an aqueous solution sufficient to cause the drug-loaded microbeads of the drug-loaded microbead composition to swell, whereby the drug-loaded microbeads after swelling comprise a water content of from 50% by weight to 95% by weight, based on the total weight of the drug-loaded microbeads.

Item A31: The embolization composition of Item A30, wherein the aqueous solution is a physiologically buffered saline solution.

Item A32: The embolization composition of Item A30 or A31, wherein swollen individual drug-loaded microbeads of the embolization composition comprise, based on the total weight of the swollen individual drug-loaded microbeads: from about 3% by weight to about 10% by weight water-swellable polymer material; from about 0.1% by weight to about 2.5% by weight therapeutic agent; from about 0.1% by weight to about 4.0% by weight carrier; and from about 50% by weight to about 96% by weight water.

Item A33: A method for preparing an embolization composition, the method comprising: adding a drug-loaded microbead composition according to any of Items A1-A20, or a drug-loaded microbead composition made according to the method of any one of Items A21-A25, or a drug-loaded microbead composition made according to the method of any one of Items A26-A29, to an amount of an aqueous solution sufficient to cause the drug-loaded microbeads of the drug-loaded microbead composition to swell, whereby the drug-loaded microbeads after swelling comprise a water content of from 50% by weight to 95% by weight, based on the total weight of the drug-loaded microbeads, to form an injection-ready solution; and loading the injection-ready solution into an injection device.

Item A34: The method of Item A33, further comprising allowing the drug-loaded microbeads to swell for a rehydration time of from about 5 minutes to about 60 minutes before loading the injection-ready solution into the injection device.

Item A35: The method of Item A33 or A34, wherein the aqueous solution is a physiologically buffered saline solution.

Item A36: A method for treating a disease, the method comprising: providing intravenously, to a subject in need of embolization therapy, an embolization composition according to any one of Items A30-A32.

Item A37: The method of Item A36, wherein: after the embolization composition is provided intravenously, at least a portion of the drug-loaded microbeads flow through vasculature of the subject to an embolization site and restrict blood flow through the embolization site; and the drug-loaded microbeads release to tissue at the embolization site over the course of a release period at least 90% by weight of the therapeutic agent, based on an initial amount of therapeutic agent embedded within the microbeads before the embolization composition is provided.

Item A38: The method of Item A37, wherein the release to the tissue at the embolization site includes an initial burst of release, during which of at least 10% by weight of the therapeutic agent, based on the initial amount.

Item A39: The method of Item A37 or A38, wherein the drug-loaded microbeads provide a sustained release of the therapeutic agent to the tissue over the release period.

Item A40: The method of any one of Items A37-A39, wherein the release period is at least 14 days.

Item A41: The method of any one of Items A37-A38, wherein the release period is at least 28 days.

Item A42: The method of any one of Items A36-A41, wherein the disease is a cancer.

Item A43: The method of Item A42, wherein the cancer is hepatocellular carcinoma, liver cancer, prostate cancer, or breast cancer.

Item B1: A drug-loaded microbead composition comprising: a plurality of individual microbeads of a biodegradable material; a plurality of individual vesicular agents contained within the individual microbeads or associated with the biodegradable material of the individual microbeads through ionic or non-covalent interaction, the vesicular agents comprising at least one lipid bilayer surrounding a vesicular core; and a first therapeutic agent contained within the individual vesicular agents or associated with the individual vesicular agents by ionic or non-covalent interaction; and a second therapeutic agent different from the first therapeutic agent and contained within the individual microbeads or associated with the individual microbeads through ionic or non-covalent interaction.

Item B2: The drug-loaded microbead composition of Item B1, wherein the vesicular agents comprise liposomes or ethosomes.

Item B3: The drug-loaded microbead composition of Item B1 or B2, wherein the second therapeutic agent is contained within the individual vesicular agents or associated with individual vesicular agents through ionic or non-covalent interaction.

Item B4: The drug-loaded microbead composition of any of the preceding Items B1 to B3, wherein the first therapeutic agent is hydrophilic and the second therapeutic agent is hydrophobic.

Item B5: The drug-loaded microbead composition of Item B4, wherein the first therapeutic agent is encapsulated within the vesicular core of the individual vesicular agents and the second therapeutic agent is contained within the lipid bilayer of the individual vesicular agents.

Item B6: The drug-loaded microbead composition of Item B4, wherein the second therapeutic agent is not contained within the individual vesicular agents and is associated by ionic or non-covalent interaction with the biodegradable material of the individual microbeads.

Item B7: The drug-loaded microbead composition of any of the preceding Items B1 to B6, wherein the first therapeutic agent and the second therapeutic agent are independently chosen from doxorubicin, bevacizumab, bortezomib, imatinib, seliciclib, ceritinib, everolimus, paclitaxel, sorafenib, irinotecan, idarubicin, cisplatin, and combinations thereof.

Item B8: The drug-loaded microbead composition of any of the preceding Items B1 to B7, wherein the biodegradable material is a biodegradable polymer chosen from poly (lactide-co-glycolide) (PLGA), polylactide (PLA), polyglycolide (PGA), polycaprolactone (PCL), polyhydroxyalkanoates, poly-R-3-hydroxybutyrate (poly3HB), poly-R-3-hydroxybutyrate-co-R-3-hydroxyvalerate (poly(3HB-co-3HV)), poly-R-3-hydroxybutyrate-co-4-hydroxybutyrate (poly(3HB-co-4HB)), poly-R-3 hydroxyoctanoate-co-R-3-hydroxyhexanoate (poly(3HO-co-3HH)), poly-3-hydroxy-propionate (poly(3HP)), poly-4-hydroxybutyrate (poly (4HB)), poly-5-hydroxybutyrate (poly(5HB)), poly-6-hydroxybutyrate (poly(6HB)), poly(propylene fumarate), poly(butylene succinate), poly(p-dioxanone, polyacetals, poly(ortho esters), polycarbonates, chitosan, hydroxybutyric acids, polyanhydrides and polyesters, polyphosphazenes, polyphosphoesters, lipodisq, celluloses, modified celluloses, proteins and poly(amino acids), polyethers, and co-polymers of the foregoing.

Item B9: The drug-loaded microbead composition of any of the preceding Items B1 to B8, wherein the biodegradable material is a cellulose.

Item B10: The drug-loaded microbead composition of any of the preceding Items B1 to B9, wherein the biodegradable material is a modified cellulose comprising cellulose acetate butyrate.

Item B11: The drug-loaded microbead composition of any of Items B1 to B7, wherein the biodegradable material is a lipid chosen from tricaprin, trilaurin, trimyristin, tripalmitin, tristearin, hydrogenated coco-glycerides, glyceryl monostearate, glyceryl behenate, glyceryl palmitostearate, glyceryl caprate, cetyl palmitate, stearic acid, palmitic acid, decanoic acid, behenic acid, beeswax, carnauba wax, cacao butter, and combinations thereof.

Item B12: The drug-loaded microbead composition of Item B1, wherein: the individual vesicular agents comprise liposomes; the first therapeutic agent is contained within the lipid bilayer of the individual vesicular agents; the second therapeutic agent is not contained within the individual vesicular agents and is associated by ionic or non-covalent interaction with the biodegradable material of the individual microbeads; and the biodegradable material is a cellulose.

Item B13: The drug-loaded microbead composition of Item B1, wherein: the individual vesicular agents comprise liposomes; the first therapeutic agent is contained within the lipid bilayer of the individual vesicular agents; the second therapeutic agent is encapsulated within the vesicular core of the individual vesicular agents; the first therapeutic agent is sorafenib; the second therapeutic agent is doxorubicin; and the biodegradable material is a cellulose.

Item B14: The drug-loaded microbead composition of Item B1, wherein: the individual vesicular agents comprise ethosomes; the first therapeutic agent is encapsulated within the vesicular core of the individual vesicular agents; the second therapeutic agent is not contained within the individual vesicular agents and is associated by ionic or non-covalent interaction with the biodegradable material; the first therapeutic agent is sorafenib; the second therapeutic agent is doxorubicin; and the biodegradable material is a cellulose.

Item B15: The drug-loaded microbead composition of any of the preceding Items B1 to B14, wherein the at least one lipid bilayer comprises poly(2-methacryloyloxyethyl phosphorylcholine) (PMPC), dioleoyl phosphatidylserine (DOPS), dioleoyl phosphatidylethanolamine (DOPE), and cholesterol.

Item C1: A drug-loaded microbead composition according to any of Items B1 to B15, comprising as a further attribute any feature of any drug-loaded microbead composition according to any of Items A1 to A20.

Item C2: A drug-loaded microbead composition according to any of Items A1 to A20, comprising as a further attribute any feature of any drug-loaded microbead composition according to any of Items B1 to B15.

Item C3: A drug-loaded microbead composition comprising a combination or mixture of microbeads from a drug-loaded microbead composition according to any of Items A1 to A20 and microbeads from a drug-loaded microbead composition according to any of Items B1 to B15.

Unless otherwise defined, all technical and scientific terms used herein have the same meaning as commonly understood by one of ordinary skill in the art to which the invention belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. One of ordinary skill in the art will understand that any numerical values inherently contain certain errors attributable to the measurement techniques used to ascertain the values.

It is noted that terms like "preferably," "commonly," and "typically" are not utilized herein to limit the scope of the claims or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is used herein to represent the inherent degree of uncertainty that may be attributed to any quantitative comparison, value, measurement, or other representation. The term "substantially" is used herein also to represent the degree by which a quantitative representation may vary from a stated reference without resulting in a change in the basic function of the subject matter at issue. As such, it is used to represent the inherent degree of uncertainty that may be attributed to any quantitative comparison, value, measurement, or other representation, referring to an arrangement of elements or features that, while in theory would be expected to exhibit exact correspondence or behavior, may in practice embody something less than exact.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

The invention claimed is:

1. A drug-loaded microbead composition comprising:
    a plurality of individual microbeads of a biodegradable material;
    a plurality of individual vesicular agents contained within the individual microbeads or associated with the biodegradable material of the individual microbeads through ionic or non-covalent interaction, the vesicular agents comprising at least one lipid bilayer comprising a phospholipid and surrounding a vesicular core, wherein the vesicular agents comprise liposomes or ethosomes; and a first therapeutic agent contained within the individual vesicular agents or associated with the individual vesicular agents by ionic or non-covalent interaction; and a second therapeutic agent different from the first therapeutic agent and contained within the individual microbeads or associated with the individual microbeads through ionic or non-covalent interaction.

2. The drug-loaded microbead composition of claim 1, wherein the second therapeutic agent is contained within the individual vesicular agents or associated with individual vesicular agents through ionic or non-covalent interaction.

3. The drug-loaded microbead composition of claim 1, wherein the first therapeutic agent is hydrophilic and the second therapeutic agent is hydrophobic.

4. The drug-loaded microbead composition of claim 3, wherein the first therapeutic agent is encapsulated within the vesicular core of the individual vesicular agents and the second therapeutic agent is contained within the lipid bilayer of the individual vesicular agents.

5. The drug-loaded microbead composition of claim 3, wherein the second therapeutic agent is not contained within the individual vesicular agents and is associated by ionic or non-covalent interaction with the biodegradable material of the individual microbeads.

6. The drug-loaded microbead composition of claim 1, wherein the first therapeutic agent and the second therapeutic agent are independently chosen from doxorubicin, bevacizumab, bortezomib, imatinib, seliciclib, ceritinib, everolimus, paclitaxel, sorafenib, irinotecan, idarubicin, cisplatin, and combinations thereof.

7. The drug-loaded microbead composition of claim 1, wherein the biodegradable material is selected from the group consisting of biodegradable polymers and lipids, wherein:
the biodegradable polymers are chosen from poly(lactide-co-glycolide) (PLGA), polylactide(PLA), polyglycolide (PGA), polycaprolactone (PCL), polyhydroxyalkanoates, poly-R-3-hydroxybutyrate (poly3HB), poly-R-3-hydroxybutyrate-co-R-3-hydroxyvalerate (poly(3RB-co-3HV)), poly-R-3-hydroxybutyrate-co-4-hydroxybutyrate (poly(3HB-co-4HB)), poly-R-3-hydroxyoctanoate-co-R-3-hydroxyhexanoate (poly(3HO-co-3HH)), poly-3-hydroxypropionate (poly(3HP)), poly-4-hydroxybutyrate (poly(4HB)), poly-5-hydroxybutyrate (poly(5H-1B)), poly-6-hydroxybutyrate (poly(6HB)), polypropylene fumarate), poly(butylene succinate), poly(p-dioxanone, polyacetals, poly(ortho esters), polycarbonates, chitosan, hydroxybutyric acids, polyanhydrides, polyphosphazenes, polyphosphoesters, celluloses or modified celluloses, proteins, poly(amino acids), polyethers, and co-polymers of the foregoing; and
the lipids are chosen from tricaprin, trilaurin, trimyristin, tripalmitin, tristearin, hydrogenated coco-glycerides, glyceryl monostearate, glyceryl behenate, glyceryl palmitostearate, glyceryl caprate, cetyl palmitate, stearic acid, palmitic acid, decanoic acid, behenic acid, beeswax, carnauba wax, cacao butter, and combinations thereof.

8. The drug-loaded microbead composition of claim 1, wherein:
the individual vesicular agents comprise liposomes;
the first therapeutic agent is contained within the lipid bilayer of the individual vesicular agents;
the second therapeutic agent is not contained within the individual vesicular agents and is associated by ionic or non-covalent interaction with the biodegradable material of the individual microbeads; and
the biodegradable material is a cellulose.

9. The drug-loaded microbead composition of claim 1, wherein:
the individual vesicular agents comprise liposomes;
the first therapeutic agent is contained within the lipid bilayer of the individual vesicular agents;
the second therapeutic agent is encapsulated within the vesicular core of the individual vesicular agents;
the first therapeutic agent is sorafenib;
the second therapeutic agent is doxorubicin; and
the biodegradable material is a cellulose.

10. The drug-loaded microbead composition of claim 1, wherein:
the individual vesicular agents comprise ethosomes;
the first therapeutic agent is encapsulated within the vesicular core of the individual vesicular agents;
the second therapeutic agent is not contained within the individual vesicular agents and is associated by ionic or non-covalent interaction with the biodegradable material;
the first therapeutic agent is sorafenib;
the second therapeutic agent is doxorubicin; and
the biodegradable material is a cellulose.

11. The drug-loaded microbead composition of claim 1, wherein the at least one lipid bilayer comprises a combination of poly(2-methacryloyloxyethyl phosphorylcholine) (PMPC), dioleoyl phosphatidylserine (DOPS), dioleoyl phosphatidylethanolamine (DOPE), and cholesterol.

* * * * *

UNITED STATES PATENT AND TRADEMARK OFFICE
CERTIFICATE OF CORRECTION

| | | |
|---|---|---|
| PATENT NO. | : 11,590,080 B2 | Page 1 of 1 |
| APPLICATION NO. | : 16/913314 | |
| DATED | : February 28, 2023 | |
| INVENTOR(S) | : Elena Afonina et al. | |

It is certified that error appears in the above-identified patent and that said Letters Patent is hereby corrected as shown below:

In the Claims

In Column 39, Line(s) 50, Claim 7, delete "polypropylene fumarate)" and insert --poly(propylene fumarate)--, therefor.

In Column 39, Line(s) 51, Claim 7, delete "poly(p-dioxanone" and insert --poly(p-dioxanone)--, therefor.

Signed and Sealed this
Second Day of May, 2023

*Katherine Kelly Vidal*

Katherine Kelly Vidal
*Director of the United States Patent and Trademark Office*